United States Patent [19]

Nadler et al.

[11] Patent Number: 5,877,282

[45] Date of Patent: Mar. 2, 1999

[54] PEPTIDE INHIBITORS OF NUCLEAR PROTEIN TRANSLOCATION HAVING NUCLEAR LOCALIZATION SEQUENCES AND METHODS OF USE THEREOF

[75] Inventors: Steven G. Nadler, Princeton, N.J.; Jeffrey S. Cleaveland, Seattle, Wash.; James Blake, Seattle, Wash.; Omar K. Haffar, Seattle, Wash.

[73] Assignee: Bristol-Myers Squibb Company, New York, N.Y.

[21] Appl. No.: 928,958

[22] Filed: Sep. 12, 1997

Related U.S. Application Data

[60] Provisional application No. 60/026,978 Sep. 20, 1996.

[51] Int. Cl.$^6$ .................................................. C07K 14/00
[52] U.S. Cl. .................................................. 530/350
[58] Field of Search ................................. 530/350

[56] References Cited

FOREIGN PATENT DOCUMENTS

| | | |
|---|---|---|
| 0 359 347B1 | 12/1992 | European Pat. Off. . |
| WO 94/04696 | 3/1994 | WIPO . |
| WO 95/24928 | 9/1995 | WIPO . |
| WO 95/31999 | 11/1995 | WIPO . |
| WO 95/34295 | 12/1995 | WIPO . |

OTHER PUBLICATIONS

Berlos et al., "Conformational and Associative Behaviours of the Third Helix of Antennapedia Homeodomain in Membrane–Mimetic Environments," *Eur. J. Biochem* 242:372–386 (1996).

Hinkes et al., "Organization and Promoter Acitivity of the Mouse Syndecan–1 Gene," *The Journal of Biological Chemistry* 268:(15)11440–11448(1993).

Imamura et al, "Identification of a Heparin–Binding Growth Factor–I Nuclear Translocation Sequence by Deletion Mutation Analysis," *Journal of Biological Chemistry* 267:(8)5676–5679 (1992).

Kentrup et al., "Dyrk, a Dual Specificity Protein Kinase With Unique Structural Features Whose Activity is Dependent on Tyrosine Residues Between Subdomains VII and VIII," *The Journal of Biological Chemistry* 271:(7)3488–3498 (1996).

Mukaigawa et al., "Two Signal Mediate Nuclear Localization of Influenza Virus (A/WSN/33) Polymerase Basic Protein 2," *Journal Virology* 65:(1)253–254 (1991).

Perez et al., "Antennapedia Homeobox as a Signal for the Cellular Internalization and Nuclear Addressing of a Small Exogenous Peptide," *Journal of Cell Science* 102:717–722 (1992).

Theodore et al., "Intraneuronal Delivery of Protein Kinase C Pseudosubstrate Leads to Growth Cone Collapse," *The J. of Neuroscience* 15(11):7158–7167 (1995).

*Primary Examiner*—Karen Cochrane Carlson
*Attorney, Agent, or Firm*—Robins & Associates

[57] ABSTRACT

Novel polypeptide inhibitors of cytoplasmic protein nuclear translocation are disclosed. The inhibitors are comprised of a signal sequence and at least two nuclear localization sequences. The polypeptides are useful as immunosuppression, antiviral and antitumor agents.

17 Claims, 19 Drawing Sheets

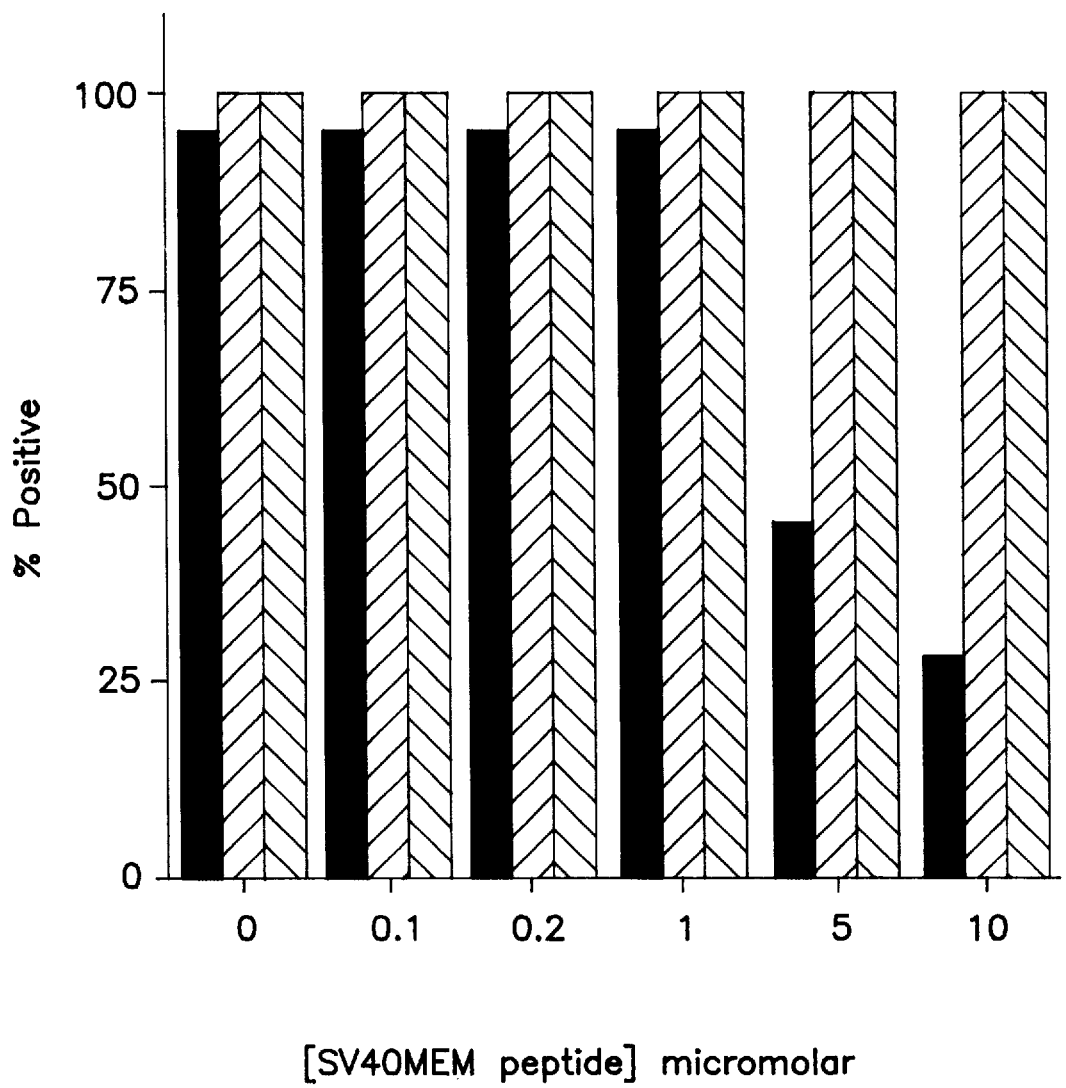
FIG. IA

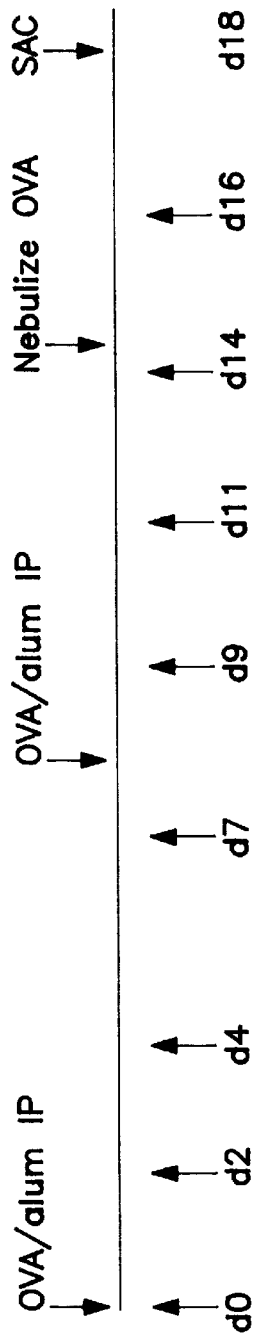
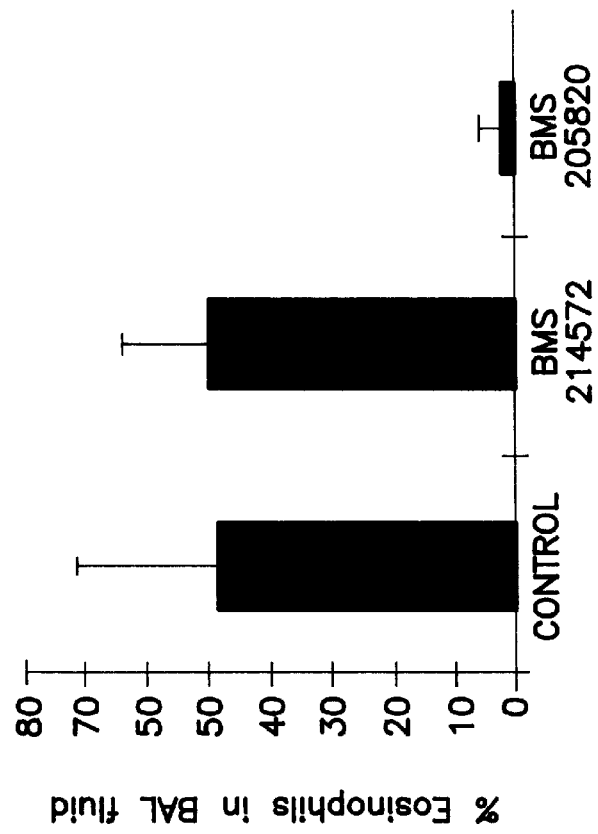
FIG. 15A
FIG. 15B

PEPTIDE INHIBITORS OF NUCLEAR PROTEIN TRANSLOCATION HAVING NUCLEAR LOCALIZATION SEQUENCES AND METHODS OF USE THEREOF

CROSS-REFERENCE TO RELATED APPLICATION

This application is related to provisional patent application Ser. No. 60/026,978, filed Sep. 20, 1996, now abandoned from which priority is claimed under 35 USC §119 (e)(1) and which is incorporated herein by reference in its entirety.

TECHNICAL FIELD

The present invention relates generally to polypeptide inhibitors of gene expression. More particularly, the invention relates to polypeptide inhibitors of nuclear protein translocation which have gene expression modulating activity, immunosuppressive activity, antiviral activity, and antitumor activity.

BACKGROUND OF THE INVENTION

Nuclear transport is essential to a number of biological processes including gene expression and cell division, as well as to viral replication, tumorigenesis and tumor cell proliferation. The mechanism of nuclear transport has only recently been characterized in detail and has been shown to involve a number of discrete steps. Proteins that are destined to be transported into the nucleus contain within their amino acid sequence a short stretch of amino acids termed a nuclear localization sequence ("NLS"). These sequences are generally basic in nature, however, there has been no consensus sequence identified. Thus, there is a wide variety of these sequences that appear to be specific for particular proteins.

Within the cell, these NLSs may be either masked or unmasked by accessory proteins or by conformational changes within the NLS-containing protein. An NLS may be masked because it is buried in the core of the protein and not exposed on the surface of the protein. Unmasking of NLSs, and nuclear translocation of cytoplasmic proteins may be triggered by phosphorylation, dephosphorylation, proteolytic digestion, subunit association or dissociation of an inhibitory subunit, or the like. Accordingly, the masking and unmasking of NLSs provides a mechanism by which the transport of these cytoplasmic proteins into the nucleus may be regulated.

Nuclear translocation of transcription factors requires the presence of an unmasked or activated NLS in the nucleus-targeted protein. The binding of certain ligands to cell surface receptors activates the nuclear translocation of cytoplasmic transcription factors. Once in the nucleus, these transcription factors exert gene expression modulatory activity.

NF-κB is a ubiquitous transcription factor found in various levels and states of activation in different cell types. NF-κB is composed of several different subunits including p65, p50, c-rel, p52 and p105. Recent studies suggest that distinct NF-κB complexes contribute to the regulatory control of gene transcription. The function and regulation of NF-κB has been most well-characterized in lymphocytic cells. In these cells, there is a wide variety of target genes, e.g., immunoregulatory genes, that are regulated by NF-κB including κ Ig light chains. Such genes include those that encode the interleukin-2α ("IL-2α") receptor, interleukin-2 ("IL-2"), interleukin-6 ("IL-6"), tumor necrosis factor-α ("TNF-α"), and the like.

In unstimulated cells, a major form of NF-κB is a heterodimer of p50 and p65 (RelA) subunits. Nonactive NF-κB is retained in the cytoplasm as an inactive complex by inhibitory proteins such as IκBα, β and γ. When cells are appropriately stimulated, e.g., by a proinflammatory stimulus such as a cytokine, the IκBs are degraded, thereby releasing free NF-κB dimers, which translocate to the nucleus and activate target genes, e.g., lymphokine genes and other immunoregulatory genes. This response is transient and is terminated through delayed NF-κB-mediated IκBα induction.

Recently it has been demonstrated that glucocorticoids exert their immunosuppressive activity by inhibiting NF-κB nuclear translocation. Scheinman et al. (1995) *Science* 270:283–286 and Auphan et al. (1995) *Science* 270:286–290 independently demonstrated that the inhibition is mediated by an increase in the induction by glucocorticoids of IκB inhibitory proteins. These investigators proposed that inhibitors of NF-κB may be useful immunosuppressive and anti-inflammatory agents. Such an NF-κB nuclear translocation inhibitor, comprising an NLS from the p50 subunit of NF-κB attached to a membrane-permeable polypeptide motif, was described in Lin et al. (1995) *J. Biol. Chem.* 270:14255–14258.

Nuclear translocation of proteins other than endogenous transcription factors and other cytoplasmic proteins also depends on the presence of an activated or unmasked NLS. For example, nuclear translocation of the retroviral preintegration complex is a crucial step in human immunodeficiency virus type-1 ("HIV-1") replication in nondividing cells such as monocytes and growth-arrested T cells. Such translocation is dependent on the presence of an NLS in the N-terminal portion of HIV matrix antigen ("MA") p17. Indeed, the HIV-1 enhancer contains tandem binding sites for NF-κB that can be essential for virus replication (Ross et al. (1991) *J. Virol.* 65:4350–4358; Parrott et al. (1991) *J. Virol* 65:1414–1419). Nuclear translocation of the HIV-1 preintegration complex can be partially inhibited by an excess of the SV40 large T antigen NLS (Gulizia et al. (1994) *J. Virol.* 68:2021–2025). Furthermore, Dubrovsky et al. (1995) *Molecular Med.* 2:217–230 reported that a series of compounds capable of binding to and reacting with the HIV-1 MA p17 NLS inhibit HIV-1 replication in human monocytes.

In addition, tumorigenesis and tumor cell proliferation are regulated by the expression of oncoproteins, many of which are cytoplasmic transcription factors that are translocated into the nucleus by virtue of the presence of an NLS. Miller et al. (1996) *J. Cell Biochemistry* 60:560.

Accordingly, inhibitors of nuclear translocation of cytoplasmic proteins would be useful as gene expression modulating agents, immunoregulatory agents, antiviral agents, antitumor agents, and the like.

SUMMARY OF THE INVENTION

The present invention provides for a polypeptide that can be introduced into an intact cell for the purpose of inhibiting the nuclear translocation of a cytoplasmic protein. The polypeptide contains at least two NLSs and an amino acid sequence that can deliver the polypeptide through the cytoplasmic membrane into the cell. The inventors herein have found that such a polypeptide exhibits surprisingly superior characteristics compared to a polypeptide having only one NLS.

Accordingly, in one embodiment, the invention is directed to a polypeptide comprising a signal sequence peptide and at least two NLSs covalently attached thereto.

In another embodiment, the invention is directed to a method of introducing an exogenous polypeptide comprising an NLS into an intact cell to inhibit nuclear translocation of a cellular protein. The method includes providing a polypeptide comprising a signal sequence peptide and at least two NLSs as described above, and contacting the cell with the polypeptide for a period of time effective to introduce the exogenous polypeptide into the cell.

In still another embodiment, the invention is directed to a method of suppressing an immune response of a subject comprising administering to the subject an immunosuppressive amount of a polypeptide comprising a signal sequence peptide and at least two NLSs.

In a further embodiment, the invention is directed to a method of treating or preventing a viral infection in an individual comprising administering to the individual an effective antiviral amount of a polypeptide inhibitor of nuclear translocation of a cellular protein, said inhibitor comprising a signal sequence peptide and at least two NLSs.

In yet a further embodiment, the invention is directed to a method of transcriptionally modulating the expression of cellular genes comprising contacting a target cell with an inhibitor of nuclear translocation of a cellular protein, wherein the inhibitor comprises a signal sequence peptide and at least two NLSs.

These and other embodiments of the subject invention will readily occur to those of ordinary skill in the art in view of the disclosure herein.

BRIEF DESCRIPTION OF THE FIGURES

FIG. 1A is a graphical representation of the effect of PKKKRKVAAVALLPAVLLALLAPKKKRKVC (SEQ ID NO:1) (the "SV40MEM" polypeptide) on lipopolysaccharide ("LPS")-stimulated surface antigen expression in 70Z/3 murine leukemia pre-B cells (solid bar: κ Ig light chain; stippled bar: IL-2α receptor; striped bar: CD45).

FIG. 15A is a time line depicting the administration scheme for the intraperitoneal injection of ovalbumin (OVA), nebulized OVA, BMS 205820 and C-MYCMEM. FIG. 15B shows the % eosinophils in lung following the treatment outlined in FIG. 15A.

DETAILED DESCRIPTION

Figure 1B:
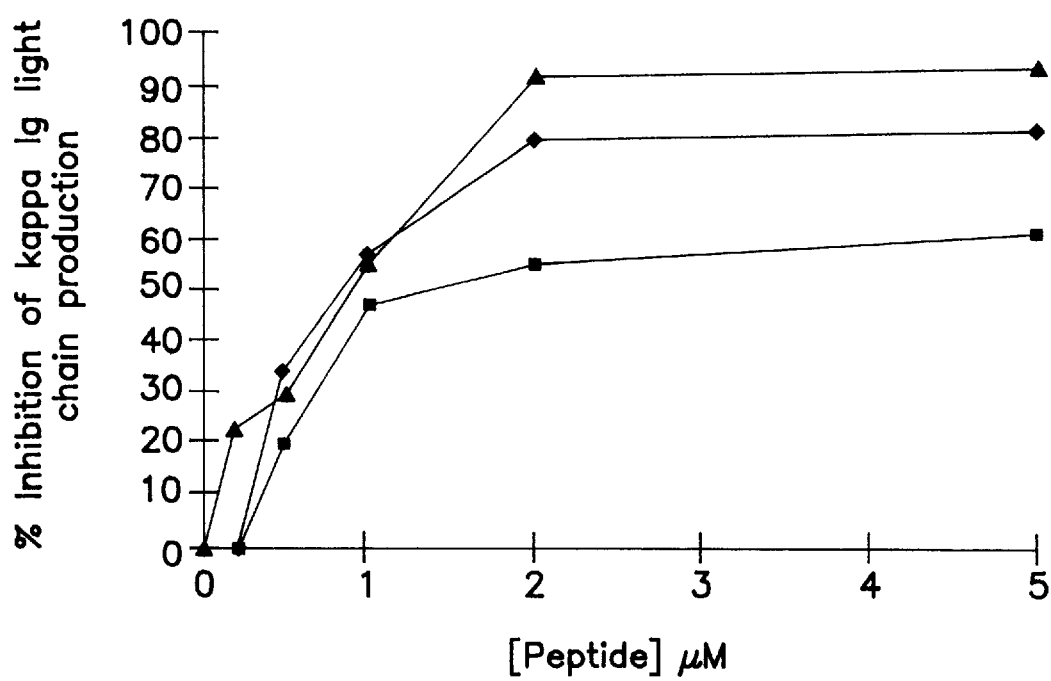
FIG. 1B is a graphical representation of the effect of three inhibitory polypeptides on LPS-stimulated κ Ig light chain production in 70Z/3 murine leukemia pre-B cells (diamonds: the SV40MEM polypeptide; squares: KKKYKAAVALLPAVLLALLAKKKYKC (SEQ ID NO:2) (the "HIV-1MEM" polypeptide); triangles: AKRVKLAAVALLPAVLLALLAKRVKLC (SEQ ID NO:3) (the "C-MYCMEM" polypeptide)).

The practice of the present invention will employ, unless otherwise indicated, conventional techniques of protein chemistry and biochemistry, molecular biology, microbiology and recombinant DNA technology, which are within the skill of the art. Such techniques are explained fully in the literature. See, e.g., Sambrook, Fritsch & Maniatis, *Molecular Cloning: A Laboratory Manual*, Second Edition (1989); *DNA Cloning*, Vols. I and II (D. N. Glover ed. 1985); *Oligonucleotide Synthesis* (M. J. Gait ed. 1984); *Nucleic Acid Hybridization* (B. D. Hames & S. J. Higgins eds. 1984); *Animal Cell Culture* (R. K. Freshney ed. 1986); *Immobilized Cells and Enzymes* (IRL press, 1986); Perbal, B., *A Practical Guide to Molecular Cloning* (1984); the series, *Methods In Enzymology* (S. Colowick and N. Kaplan eds., Academic Press, Inc.).

All patents, patent applications and publications cited herein, whether supra or infra, are hereby incorporated by reference in their entirety.

As used in this specification and the appended claims, the singular forms "a," "an" and "the" include plural references unless the content clearly dictates otherwise.

A. Definitions

In describing the present invention, the following terms will be employed, and are intended to be defined as indicated below.

As used herein, the term "signal sequence" or "signal sequence peptide" is used to indicate a peptide that is capable of directing the movement of the polypeptide of which it is a part through a cell membrane. In particular, the term is used to indicate a peptide that directs the movement of a polypeptide across the cytoplasmic membrane into the cell. The term "signal sequence" is intended to encompass not only the signal sequence of a particular polypeptide, but also fragments or derivatives thereof that are capable of delivering a polypeptide through a cell membrane. A "signal sequence" may be composed of L- or D-amino acids.

The terms "nuclear localization sequence" and "NLS" are used interchangeably to indicate a peptide that directs the transport of a protein with which it is associated from the cytoplasm of a cell across the nuclear envelope barrier. The term "NLS" is intended to encompass not only the nuclear localization sequence of a particular peptide, but also derivatives thereof that are capable of directing translocation of a cytoplasmic polypeptide across the nuclear envelope barrier. NLSs are capable of directing nuclear translocation of a polypeptide when attached to the N-terminus, the C-terminus, or both the N- and C-termini of the polypeptide. In addition, a polypeptide having an NLS coupled by its N- or C-terminus to amino acid side chains located randomly along the amino acid sequence of the polypeptide will be translocated. Adam et al. (1990) *J. Cell. Biol.* 111:807–818. "Nuclear localization sequences" may be composed of D- or L-amino acids.

By "interchangeably flanked at its amino- and carboxy-termini by a first and a second NLS" is intended to mean that the first or second NLS may be located at either the amino- or carboxy-terminus of the signal sequence polypeptide.

An "inhibitor of nuclear translocation" is a polypeptide composed of a signal sequence peptide and at least two NLSs which inhibits, e.g., either decreases or halts, nuclear localization of a cytoplasmic protein. Preferably, the polypeptide comprises a signal sequence peptide interchangeably flanked at its amino- and carboxy-termini by a first and a second NLS. The NLSs at the N- and C-termini may be the same or different. In one preferred embodiment, the signal sequence peptide and the NLSs are each composed of L-amino acids. In another preferred embodiment, the signal sequence peptide and the NLSs are each composed of D-amino acids.

A "derivative" of a polypeptide is intended to include homologous polypeptides in which conservative amino acid substitutions have been made, as well as to include other amino acid substitutions that result in a polypeptide that retains its function, e.g., as a signal sequence peptide, an NLS, or an inhibitor of nuclear localization. A "derivative" of a peptide may be a peptide mimetic.

"Peptide mimetics" are structures which serve as substitutes for peptides in interactions with acceptor molecules (see Morgan et al. (1989) *Ann. Reports Med. Chem.* 24:243–252 for a review of peptide mimetics). Peptide mimetics, as used herein, include synthetic structures which may or may not contain amino acids and/or peptide bonds, but retain the structural and functional features of a peptide ligand. The term, "peptide mimetics" also includes peptoids and oligopeptoids, which are peptides or oligomers of N-substituted amino acids (Simon et al. (1972) *Proc. Natl. Acad. Sci. USA* 89:9367–9371). Further included as peptide mimetics are peptide libraries, which are collections of peptides designed to be of a given amino acid length and representing all conceivable sequences of amino acids corresponding thereto. Methods for the production of peptide mimetics are described more fully below.

Two polypeptide sequences are "substantially homologous" when at least about 85% (preferably at least about 85% to 90%, and most preferably at least about 95%) of the nucleotides or amino acids match over a defined length of the molecule. As used herein, substantially homologous also refers to sequences showing identity to the specified polypeptide sequence.

The terms "polypeptide", "peptide" and "protein" are used interchangeably and refer to any polymer of amino acids (dipeptide or greater) linked through peptide bonds. Thus, the terms "polypeptide", "peptide" and "protein" include oligopeptides, protein fragments, analogues, muteins, fusion proteins and the like.

The following single-letter amino acid abbreviations are used throughout the text:

| Alanine | A | Arginine | R |
|---|---|---|---|
| Asparagine | N | Aspartic acid | D |
| Cysteine | C | Glutamine | Q |
| Glutamic acid | E | Glycine | G |
| Histidine | H | Isoleucine | I |
| Leucine | L | Lysine | K |
| Methionine | M | Phenylalanine | F |
| Proline | P | Serine | S |
| Threonine | T | Tryptophan | W |
| Tyrosine | Y | Valine | V |

By an "isolated polypeptide" is meant a polypeptide which is devoid of, in whole or part, tissue or cellular components with which the protein is normally associated in nature. Thus, a polypeptide contained in a tissue extract would constitute an "isolated" polypeptide, as would a polypeptide synthetically or recombinantly produced.

By "mammalian subject" is meant any member of the class Mammalia, including, without limitation, humans and non-human primates, such as chimpanzees and other apes and monkey species; farm animals such as cattle, sheep, pigs, goats and horses; domestic mammals such as dogs and cats; and laboratory animals including rodents such as mice, rats and guinea pigs. The term does not denote a particular age. Thus, adult, newborn and fetal mammals are intended to be covered.

The term "treatment" as used herein refers to either (i) the prevention of infection or reinfection (prophylaxis), or (ii) the reduction or elimination of symptoms of the disease of interest (therapy).

B. General Methods

Central to the present invention is the discovery of polypeptide molecules that inhibit nuclear localization of cytoplasmic proteins. These molecules comprise a signal sequence peptide and at least two NLSs. The polypeptide inhibitors, and derivatives thereof, provide useful tools for introducing an exogenous polypeptide comprising an NLS into an intact cell to inhibit nuclear translocation of a cellular protein, for studying the role of nuclear translocation in the regulation of cellular processes.

In addition, since the nuclear translocation of certain cellular peptides is required for the host organism to mount an immune response, the polypeptide inhibitors are useful as immunosuppression agents. Immune responses are typically manifested by the expression of antibodies, the production of a number of cytokines, and/or the expression of cell surface receptors. Thus, inhibition of immune responses by the inhibitory peptides can take the form of: inhibition of antibody production, including the production of antibody component peptides such as a κ light chain polypeptide; inhibition of cytokine production, including such cytokines as interleukin-1, interleukin-2, interleukin-4, interleukin-6, interleukin-10, tumor necrosis factor, or granulocyte-macrophage colony-stimulating factor; and/or the inhibition of the expression of cell-surface receptors such as an interleukin-2 receptor, gp39, CD40, CD45, CD80, CD86, ICAM, ELAM, major histocompatibility complex ("MHC") class II, or VCAM. Clark et al. (1994) *Nature* 367:425.

By virtue of their immunosuppressive activities, the polypeptide inhibitors of the present invention are useful in the treatment of a wide variety of immune disorders, including but not limited to, the treatment of autoimmune diseases such as rheumatoid arthritis, multiple sclerosis, juvenile-onset diabetes, systemic lupus erythematosus (SLE), autoimmune uveoretinitis, autoimmune vasculitis, bullous pemphigus, myasthenia gravis, autoimmune thyroiditis or Hashimoto's disease, Sjogren's syndrome, granulomatous orchitis, autoimmune oophoritis, Crohn's disease, sarcoidosis, rheumatic carditis, ankylosing spondylitis, Grave's disease, and autoimmune thrombocytopenic purpura (see e.g., Paul, W. E. (1993) *Fundamental Immunology*, Third Edition, Raven Press, New York, Chapter 30, pp. 1033–1097; and Cohen et al. (1994) *Autoimmune Disease Models*, A Guidebook, Academic Press, 1994).

Similarly, the polypeptide inhibitors of the present invention are useful for treating physical symptoms manifested by responses to allergens which can initiate a state of hypersensitivity, or which can provoke a hypersensitivity reaction in a subject already sensitized with the allergen. Such physical symptoms include asthma, joint swelling, urticaria, and the like. Additionally, due to their immunosuppressive properties, the polypeptide inhibitors of the present invention are useful in the treatment of sepsis and in the prevention of septic shock, a potentially lethal condition caused by the uncontrolled production of certain cytokines due to the presence of endotoxins, such as lipopolysaccharide (LPS), from extracellular bacteria.

Furthermore, since many viruses, e.g., herpes virus, cytomegalovirus, retroviruses, and the like, make use of the host cell's nuclear translocation machinery, the inhibitory polypeptides are useful as antiviral agents. In addition, since tumorigenesis and tumor cell proliferation appear to be mediated by the expression of oncogenes to make oncoproteins, many of which are transcription factors that are translocated into the nucleus, Miller et al. (1996), supra, the polypeptide inhibitors, or derivatives thereof, can be used to suppress tumor growth.

The claimed inhibitors include sequences of amino acids that comprise signal sequences from such polypeptides as the antennapedia homeodomain, FGF, HIV Tat, or Hsc70, and derivatives or mimetics thereof capable of delivering the inhibitor through the cytoplasmic membrane into the cell. Preferred signal sequences include RQIKIWFQNRRMKWKK (SEQ ID NO:7), AAVALLPAVLLALLA (SEQ ID NO:8), AAVALLPAVLLALLAP (SEQ ID NO:4), CFITKALGISYGRKKRRQRRRPPQGSQTH (SEQ ID NO:9), and the like, or derivatives or mimetics thereof capable of delivering the inhibitor through the cytoplasmic membrane into the cell.

Candidate signal sequences can be tested for their ability to direct the translocation of proteins across cell membranes, for example, by monitoring the localization of exogenous detectably labeled proteins into the cell cytoplasm. Lin et al. (1995), supra, describe the use of radiolabeled proteins. In vitro nuclear peptide import can be measured using NLS peptides coupled to a fluorescent protein by methods described in Adam et al. (1990), supra.

The polypeptide inhibitor further comprises at least two NLSs. The NLSs can be covalently bonded to the N-terminus, to the C-terminus, to both the N- and C-termini of the signal sequence polypeptide, to amino acid side chains located along the amino acid sequence of the signal sequence polypeptide, or any combination thereof. Preferably, the signal sequence polypeptide is interchangeably flanked at its amino- and carboxy-termini by a first and a second NLS. The first and second NLSs may be the same or different. A discussion of NLSs and a list of NLSs can be found in Boulikas (1993) *Crit. Rev. Eukaryotic Gene Expression* 3:193–227, and references cited therein.

Approaches for identifying NLSs include: (1) gene fusion experiments between a candidate NLS-coding DNA segment and the gene coding for a cytoplasmic protein (see, e.g., Silver et al. (1984) *Proc. Natl. Acad. Sci. U.S.A.* 81:5951; Moreland et al. (1987) *Mol. Cell. Biol.* 7:4048; and Picard et al. (1987) *EMBO J.* 6:3333); (2) nuclear import of nonnuclear proteins conjugated to synthetic NLS peptides (see, e.g., Goldfarb et al. (1986) *Nature* 322:641; Markland et al. (1987) *Mol. Cell. Biol.* 7:4255; and Chelsky et al. (1989) *Mol. Cell. Biol.* 9:2487); and (3) site-directed mutagenesis of a specific segment of a nuclear protein, resulting in its cytoplasmic retention (see, e.g., Greenspan et al. (1988) *J. Virol.* 62:3020; van Etten et al. (1989) *Cell* 58:669; and Boulukos et al. (1989) *Mol. Cell. Biol.*9:5718).

Preferred NLSs include PKKKRKV (SEQ ID NO:10) and KKKRKVC (SEQ ID NO:11) from the SV40 large T antigen (see, Kalderon et al. (1984) *Cell* 39:499), GKKRSKA (SEQ ID NO:12) from yeast histone H2B (see, Moreland et al. (1987) *Mol. Cell. Biol.* 7:4048), KRPRP (SEQ ID NO:13) from adenovirus E1A (see, Lyons et al. (1987) *Mol. Cell. Biol.* 7:2451), GNKAKRQRST (SEQ ID NO:14) from the v-rel oncogene of the avian reticuloendotheliosis retrovirus strain T (see, Gilmore et al. (1988) *J. Virol.* 62:703), GGAAKRVKLD (SEQ ID NO:15) from the human c-myc oncoprotein (see, Chelsky et al. (1989) *Mol. Cell. Biol.* 9:2487), SALIKKKKKMAP (SEQ ID NO:16) from the murine c-abl (IV) gene product (see, Van Etten et al. (1989)

Cell 58:669), RKLKKLGN (SEQ ID NO:17) from the human or rat androgen receptor (see, Guiochon-Mantel et al. (1989) Cell 57:1147), PQPKKKP (SEQ ID NO:18) from protein p53 (see, Dang et al. (1989) J. Biol. Chem. 264:18019)), ASKSRKRKL (SEQ ID NO:19) from viral Jun, a transcription factor of the AP-1 complex (see, Chida et al. (1992) Proc. Natl. Acad. Sci. USA 89:4290), KKKYK (SEQ ID NO:20) and KKKYKC (SEQ ID NO:21), both of which are from the human immunodeficiency virus matrix protein (see, Bukrinsky et al. (1993) Nature 365:666), KSKKK (SEQ ID NO:22) from the human immunodeficiency virus matrix 2 protein (see, Bukrinsky et al. (1993), supra), AKRVKL (SEQ ID NO:6) and KRVKLC (SEQ ID NO:23) both of which are from the human c-myc oncoprotein (see, Chelsky et al. (1989), supra), and derivatives and mimetics thereof that are effective as an NLS.

The polypeptide inhibitors of the present invention may be synthesized by conventional techniques known in the art, for example, by chemical synthesis such as solid phase peptide synthesis. Such methods are known to those skilled in the art. In general, these methods employ either solid or solution phase synthesis methods, well known in the art. See, e.g., J. M. Stewart and J. D. Young, *Solid Phase Peptide Synthesis,* 2nd Ed., Pierce Chemical Co., Rockford, Ill. (1984) and G. Barany and R. B. Merrifield, *The Peptides: Analysis, Synthesis, Biology,* editors E. Gross and J. Meienhofer, Vol. 2, Academic Press, New York, (1980), pp. 3–254, for solid phase peptide synthesis techniques; and M. Bodansky, *Principles of Peptide Synthesis,* Springer-Verlag, Berlin (1984) and E. Gross and J. Meienhofer, Eds., *The Peptides: Analysis, Synthesis, Biology,* supra, Vol. 1, for classical solution synthesis.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups and any solid support are removed either sequentially or concurrently to afford the final polypeptide. By simple modification of this general procedure, it is possible to add more than one amino acid at a time to a growing chain, for example, by coupling (under condition that do not racemize chiral centers) a protected tripeptide with a properly protected dipeptide to form, after deprotection, a pentapeptide.

Typical protecting groups include t-butyloxycarbonyl (Boc), 9-fluorenylmethoxycarbonyl (Fmoc), benxyloxycarbonyl (Cbz), p-toluenesulfonyl (Tos); 2,4-dinitrophenyl, benzyl (Bzl), biphenylisopropyloxy-carboxycarbonyl, cyclohexyl, isopropyl, acetyl, o-nitrophenylsulfonyl, and the like. Of these, Boc and Fmoc are preferred.

Typical solid supports are generally cross-linked polymeric materials. These include divinylbenzene cross-linked styrene-based polymers, for example, divinylbenzene-hydroxymethylstyrene copolymers, divinylbenzene-chloromethylstyrene copolymers, and divinylbenzene-benzhydrylaminopolystyrene copolymers. The Divinylbenzene-benzhydrylaminopolystyrene copolymers, as illustrated herein using p-methyl-benzhydrylamine resin, offers the advantage of directly introducing a terminal amide functional group into the peptide chain, which function is retained by the chain when the chain is cleaved from the support.

In one preferred method, the polypeptides are prepared by conventional solid phase chemical synthesis on, for example, an Applied Biosystems, Inc. (ABI) 430A peptide synthesizer using a resin that permits the synthesis of the amide peptide form and using t-Boc amino acid derivatives (Peninsula Laboratories, Inc.) with standard solvents and reagents. Polypeptides containing either L- or D-amino acids may be synthesized in this manner. Polypeptide composition is confirmed by quantitative amino acid analysis and the specific sequence of each peptide may be determined by sequence analysis.

Alternatively, the polypeptides can be produced by recombinant DNA techniques by synthesizing DNA encoding the desired polypeptide, along with an ATG initiation codon. Once coding sequences for the desired polypeptides have been synthesized or isolated, they can be cloned into any suitable vector for expression. Numerous cloning vectors are known to those of skill in the art, and the selection of an appropriate cloning vector is a matter of choice. Examples of recombinant DNA vectors for cloning and host cells which they can transform include the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (Bacillus), pIJ61 (Streptomyces), pUC6 (Streptomyces), YIp5 (Saccharomyces), YCp19 (Saccharomyces) and bovine papilloma virus (mammalian cells). See, generally, *DNA Cloning*: Vols. I & II, supra; Sambrook et al., supra; B. Perbal, supra. Insect cell expression systems, such as baculovirus systems, can also be used and are known to those of skill in the art and described in, e.g., Summers and Smith, *Texas Agricultural Experiment Station Bulletin No.* 1555 (1987). Materials and methods for baculovirus/insect cell expression systems are commercially available in kit form from, inter alia, Invitrogen, San Diego Calif. ("MaxBac" kit).

The gene can be placed under the control of a promoter, ribosome binding site (for bacterial expression) and, optionally, an operator (collectively referred to herein as "control" elements), so that the DNA sequence encoding the desired polypeptide is transcribed into RNA in the host cell transformed by a vector containing this expression construction. The coding sequence may or may not contain a signal peptide or leader sequence. Heterologous leader sequences can be added to the coding sequence which cause the secretion of the expressed polypeptide from the host organism. Leader sequences can be removed by the host in post-translational processing. See, e.g., U.S. Pat. Nos. 4,431, 739; 4,425,437; 4,338,397.

Other regulatory sequences may also be desirable which allow for regulation of expression of the protein sequences relative to the growth of the host cell. Such regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases it may be necessary to modify the coding sequence so that it may be attached to the control sequences with the appropriate orientation; i.e., to maintain the proper reading frame. It may also be desirable to produce mutants or analogs of the polypeptide of interest. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., Sambrook et al., supra; *DNA Cloning*, Vols. I and II, supra; *Nucleic Acid Hybridization*, supra.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), Madin-Darby bovine kidney ("MDBK") cells, as well as others. Similarly, bacterial hosts such as *E. coli, Bacillus subtilis,* and Streptococcus spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda,* and *Trichoplusia ni.* The proteins may also be expressed in Trypanosomes.

Depending on the expression system and host selected, the proteins of the present invention are produced by growing host cells transformed by an expression vector described above under conditions whereby the protein of interest is expressed. The protein is then isolated from the host cells and purified. If the expression system secretes the protein into growth media, the protein can be purified directly from the media. If the protein is not secreted, it is isolated from cell lysates. The selection of the appropriate growth conditions and recovery methods are within the skill of the art. Once purified, the amino acid sequences of the proteins can be determined, i.e., by repetitive cycles of Edman degradation, followed by amino acid analysis by HPLC. Other methods of amino acid sequencing are also known in the art.

As explained above, peptide mimetics which structurally and functionally mimic the peptide inhibitors described above will also find use herein and may be generated using the following strategies and procedures. Generally, mimetics are designed based on information obtained by systematic replacement of L-amino acids by D-amino acids or, in the case of a polypeptide inhibitor that is made of D-amino acids, the systematic replacement of D-amino acids by L-amino acids, replacement of side chain moieties by a methyl group or pseudoisosteric groups with different electronic properties (see Hruby et al. (1990) *Biochem. J.* 268:249–262), and by systematic replacement of peptide bonds in the above described polypeptide inhibitors with amide bond replacements. For example, analogues containing amide bond surrogates may be used to investigate aspects of peptide structure and function, such as rotational freedom in the backbone, intra- and intermolecular hydrogen-bond patterns, modifications of local and total polarity and hydrophobicity, and oral bioavailability.

Local conformational constraints can also be introduced to determine conformational requirements for activity of a candidate polypeptide mimetic inhibitor of nuclear translocation. For example, $\beta,\beta$-disubstituted amino acids may be used to examine the effects of conformational constraints on peptide activity (see, e.g., Manning et al. (1982) *J. Med. Chem.* 25:408–414; Mosberg et al. (1983) *Proc. Natl. Acad. Sci. USA* 106:506– 512; Pelton et al. (1985) *Proc. Natl. Acad. Sci. USA* 82:236–239).

The mimetics can include isosteric amide bonds such as $\psi[CH_2S]$, $\psi[CH_2NH]$, $\psi[CSNH_2]$, $\psi[NHCO]$, $\psi[COCH_2]$ and $\psi[(E)$ or $(Z)$ $CH=CH]$ (see, for review, Spatola (1983) in "Chemistry and Biochemistry of Amino Acids, Peptides and Proteins," Volume VII, (Weinstein, ed.), Marcel Dekker, N.Y., 267–357). Structures which mimic the tetrahedral transition state associated with hydrolysis of a substrate bond can also be present and include hydroxymethylene, fluoroketone moieties and phosphoramidate transition state mimics (Bühlmayer et al. (1988) *J. Med. Chem.* 31:1839; Sham et al. (1988) *FEBS Lett.* 220:299; Matthews (1988) *Acc. Chem. Res.* 21:333). Cyclic amino acid analogues may be used to constrain amino acid residues to particular conformational states, e.g., $\alpha\alpha'$- and $\beta\beta'$-substituted cyclic amino acids such as 1-aminocyclopentanecarboxylic acid (cycloleucine) and $\beta,\beta$-cyclopentamethylene-$\beta$-mercaptopropionic acid (see Hruby et al. (1990), supra).

The mimetics can also include mimics of inhibitor peptide secondary structure—structures which can model the 3-dimensional orientation of amino acid residues into the known secondary conformations of proteins—including $\beta$-turn mimetics, such as phenoxathin ring system, and $\beta$-sheet mimics, such as epindolidione structures. Design, synthesis and conformational analysis of an $\alpha$-helix inducing template has been described (Kemp et al. (1988) *Tetrahedron Lett.* 29:4931; Kemp et al. (1988) *Tetrahedron Lett.* 29:4935).

Similarly, peptoids will find use herein. Peptoids are oligomers of N-substituted amino acids (Simon et al. (1972), supra), and can be used as motifs for the generation of chemically diverse libraries of novel molecules, which can then be tested for nuclear translocation inhibitory activity. The monomers may incorporate t-butyl-based side-chain and 9- fluorenylmethoxy-carbonyl $\alpha$-amine protection. Oligomerization of the peptoid monomers may be performed by, for example, in situ activation by either benzotriazol-1-yloxytris (pyrrolidino) phosphonium hexafluorphosphate or bromotris (pyrrolidino) phosphonium hexafluorophosphate. Other steps are identical to conventional peptide synthesis using $\alpha$-(9-fluorenylmethoxycarbonyl) amino acids. Oligopeptoids may be identified which have activities comparable to the corresponding inhibitory polypeptides and, thus, are useful as inhibitors of nuclear translocation (see Simon et al. (1992), supra).

Peptide ligands that exhibit nuclear translocation inhibitory activity can be developed by using a biological expression system (see Christian et al. (1992) *J. Mol. Biol.* 227:711–8; Devlin et al. (1990) *Science* 249:404–406; Cwirla et al. (1990) *Proc. Natl. Acad. Sci. USA* 87:6378–6382). The use of such systems allows the production of large libraries of random peptide sequences and the screening of these libraries for peptide sequences that have desired biochemical activity. The libraries may be produced by cloning synthetic DNA that encodes random peptide sequences into *Escherichia coli* expression vectors. In the filamentous phage system, foreign peptide sequences can be expressed on the surface of the infectious phage (see Smith (1985) *Science* 228:1315–1317; Parmley et al. (1988) *Gene* 73:305–318)

For example, a library may be made by ligating into an appropriate phage, a synthetic DNA fragment containing a degenerate coding sequence $(NNK)_n$, where N stands for an equal mixture of the deoxynucleotides G, A, T, and C, K stands for an equimolar mixture of G and T, and n stands for the number of amino acid residues desired in the product peptide. Phage are screened for expression of inhibitory activity. Those that express inhibitory activity can be cloned and propagated, their DNAs sequenced to determine the amino acid sequences of their expressed polypeptide which can be assessed for their ability to inhibit nuclear translocation.

Large libraries of polypeptide inhibitors can also be constructed by concurrent synthesis of overlapping peptides as described in U.S. Pat. No. 4,708,871 to Geysen. The solid support is generally a polyethylene or polypropylene rod onto which is graft polymerized a vinyl monomer containing at least one functional group to produce polymeric chains on the carrier. The functional groups are reacted to provide primary or secondary amine groups which are sequentially reacted with amino acid residues in the appropriate order to build the desired synthetic peptide using conventional methods of solid phase peptide chemistry.

Once synthesized or otherwise produced, the inhibitory activity of a candidate polypeptide or polypeptide mimetic can be tested by assessing the ability of the candidate to inhibit the lipopolysaccharide-induced nuclear translocation of NF-κB by, for example, using murine endothelial cells by the method described in Lin et al. (1995), supra.

Inhibitory polypeptides can be used in pharmaceutical compositions to treat autoimmune diseases and viral infections, or to suppress transplant rejection. In addition, the polypeptides can be administered to cancerous tissues in order to suppress tumor growth. The inhibitory polypeptides of the present invention can be formulated into therapeutic compositions in a variety of dosage forms such as, but not limited to, liquid solutions or suspensions, tablets, pills, powders, suppositories, polymeric microcapsules or microvesicles, liposomes, and injectable or infusible solutions. The preferred form depends upon the mode of administration and the particular cancer type targeted. The compositions also preferably include pharmaceutically acceptable vehicles, carriers or adjuvants, well known in the art, such as human serum albumin, ion exchangers, alumina, lecithin, buffer substances such as phosphates, glycine, sorbic acid, potassium sorbate, and salts or electrolytes such as protamine sulfate. Suitable vehicles are, for example, water, saline, dextrose, glycerol, ethanol, or the like, and combinations thereof. Actual methods of preparing such compositions are known, or will be apparent, to those skilled in the art. See, e.g., *Remington's Pharmaceutical Sciences*, Mack Publishing Company, Easton, Pa., 18th edition, 1990.

The above compositions can be administered using conventional modes of delivery including, but not limited to, intravenous, intraperitoneal, oral, intralymphatic, or subcutaneous administration. Local administration to a tumor in question, or to a site of inflammation, e.g., direct injection into an arthritic joint, will also find use with the present invention.

Therapeutically effective doses will be easily determined by one of skill in the art and will depend on the severity and course of the disease, the patient's health and response to treatment, and the judgment of the treating physician.

C. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Experimental Methods

Peptide Preparation

In general, polypeptides can be synthesized using a stepwise solid-phase synthesis method and purified on a $C_{18}$ reverse phase high performance liquid chromatography on a reverse-phase column eluted with a linear gradient of 10%–60% acetonitrile, 0.1% trifluoroacetic acid as described in Merrifield (1963) *J. Am. Chem. Soc.* 85:2149–2154 and Lin et al. (1988) *Biochemistry* 27:5640–5645.

The peptides described herein were synthesized on a Gilson AMS-422 multiple peptide synthesizer using Fmoc amino acids. Gausepohl et al. (1992) *Peptide Res.* 5:315–320. Peptides were cleaved from the resin and deprotected by a 2-hr reaction with trifluoroacetic acid/water/thioanisole/ethanedithiol (100:5:5:2.5). the peptides were precipitated from ether, redissolved in formic acid, diluted with water, and lyophilized. Purification was achieved by reverse-phase high performance liquid chromatography using a gradient of acetonitrile in 0.1% trifluoroacetic acid. All synthetic peptides were characterized by mass spectroscopy on a Bio-Ion 20 instrument and gave the expected molecular weight.

Murine 70Z/3 pre-B leukemia cells (ATCC T1D-158), H9 human lymphoma T-cells (ATCC CRL-8543), Jurkat human leukemia T-cells (ATCC T1B-152), and THP-1 human monocytic cells (ATCC T1B-202) were obtained from the American Type Culture Collection.

Expression of κ Ig, CD45, CD40, and the interleukin-2 receptor was assayed using standard enzyme-linked immunosorbent assays ("ELISAs") (see, Coligan et al. (eds.) (1991) *Current Protocols in Immunology*, Wiley & Sons, p. 2.10 or by FACS staining to measure cell-surface markers as described in Raff (1970) *Immunology* 19:637). Antibodies form cell surface markers were obtained from Pharmingen Co.

Amounts of TNF-α, IL-6, IL-8 and IL-10 were determined using the ELISA kits obtained from Genzyme following the manufacturer's instructions.

HIV-1 M1 p 24 levels were assayed using the procedures described in Smithgall et al (1995) *AIDS Res. and Human Retrovirus* 11:885. Proviral DNA content (gag) was measured using polymerase chain reaction analysis as described in Smithgall et al. (1995), supra.

2-LTR circles, a strictly nuclear form of HIV-1 DNA the expression of which indicates nuclear localization of the viral genome, was measured by as described in Bukrinsky et al (1991) *Science* 254:423.

EXAMPLE 1

Inhibition by the SV40MEM Polypeptide of κ Ig Light Chain Expression

This experiment was conducted to show that the polypeptide PKKKRKVAAVALLPAVLLALLAPKKKRKVC (SEQ ID NO:1) (the "SV40MEM" polypeptide), which comprises the hydrophobic region of the signal peptide from fibroblast growth factor and the SV40 large T antigen NLS, has immunosuppressive activity. The effect of the SV40MEM polypeptide was compared with two additional polypeptides, KKKYKAAVALLPAVLLALLAKKKYKC (SEQ ID NO:2) (the "HIV-1MEM" polypeptide), which is composed of the membrane translocation domain of FGF flanked by the NLS from the HIV-1 matrix protein and AKRVKLAAVALLPAVLLALLAKRVKLC (SEQ ID NO:3) (the "C-MYCMEM" polypeptide), which contains the NLS from the human c-myc oncoprotein (Chelsky et al. (1989), supra, and Dang et al. (1988), supra) using murine 70Z/3 pre-B cells.

Murine 70Z/3 cells (ATCC T1D-158) are a model cell line for analyzing the effects of compounds on B-cell differentiation. In response to *S. typhosa* LPS (Difco) or γ-interferon, these cells differentiate from surface κ immunoglobulin negative to κ Ig positive.

As seen in FIG. 1A, the SV40MEM polypeptide caused an approximately 75–80% inhibition of κ light chain expression in response to *S. typhosa* LPS (Difco) after a 1-hr pretreatment with the SV40MEM polypeptide. There was no effect of SV40MEM on the expression of CD45 or the interleukin-2 receptor. The maximum inhibitory effect occurred with an approximately 3-hr SV40MEM pretreatment. This inhibitory effect of the SV40MEM polypeptide can be overcome by increasing the concentration of LPS.

Figure 1C:
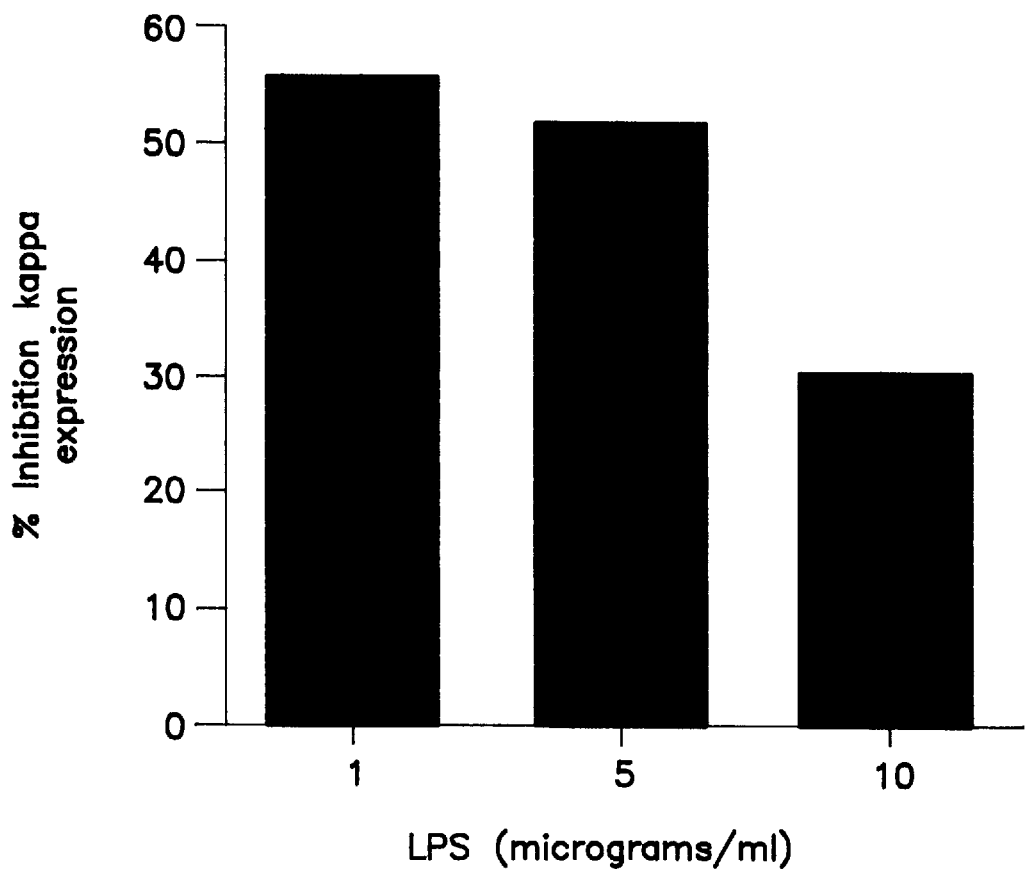
FIG. 1C is a graphical representation of the effect of increasing LPS concentrations on SV40MEM-inhibited κ Ig light chain production in 70Z/3 murine leukemia pre-B cells.

FIG. 1B depicts dose-response data for the effect of the D-amino acid form of the SV40MEM polypeptide compared with L-amino acid forms of the HIV-1MEM polypeptide and AKRVKLAAVALLPAVLLALLAKRVKLC (SEQ ID NO:3). These data show that the three polypeptides are approximately equally efficacious but that the latter two polypeptides are not as potent at inhibiting κ Ig light chain production as is SV40MEM. FIG. 1C shows that increasing the concentration of LPS can overcome the inhibitory effect of SV40MEM.

EXAMPLE 2

Inhibition by the SV40MEM Polypeptide of Cytokine Production

Figure 2:
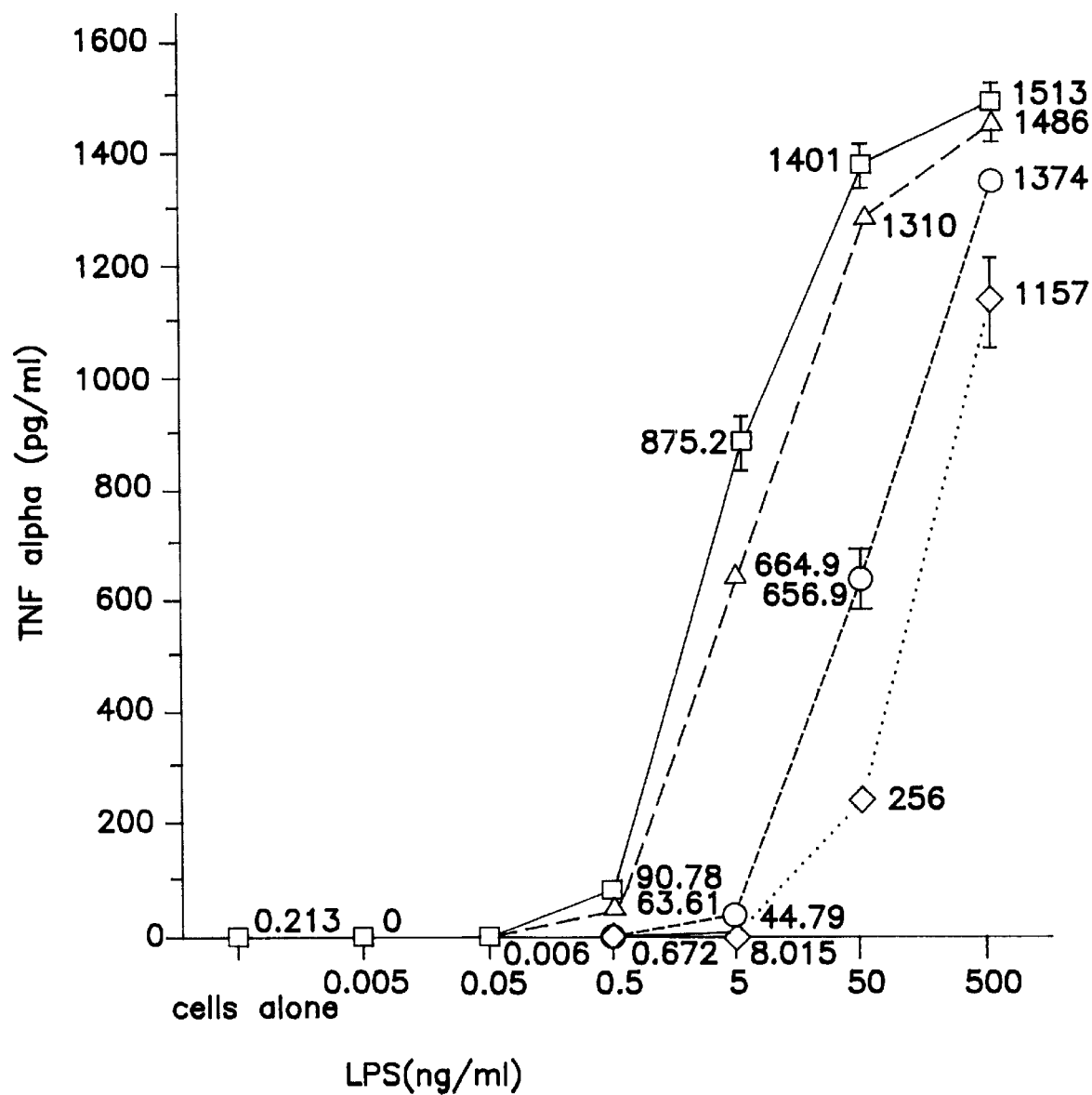
FIG. 2 is a graphical representation of the effect of the SV40MEM polypeptide on LPS-stimulated cytokine production in 70Z/3 murine leukemia pre-B cells (squares: untreated; diamonds: the SV40MEM polypeptide (10 μM); circles: the SV40MEM polypeptide (5 μM); triangles: the SV40 NLS (10 μM)).

THP-1 control cells were harvested, washed and set up in RPMI 1640, 10% fetal calf serum, at a concentration of $2.56 \times 10^6$ cells/ml. Phosphate buffered saline ("PBS") or one of the two respective polypeptides SV40MEM or SV40 (a peptide having only the SV40 large T antigen NLS sequence) were added to the cells at a concentration of 10 μM or 20 μM. The cells were then plated into a 96-well plate with 0.1 ml/well. The plate was then incubated for 2 hr at 37° C. in a 5% $CO_2$ atmosphere. Following the initial incubation, media or a titration of LPS was added to each of the wells in a volume of 0.1 ml. Thus, the final concentrations of polypeptides were 5 μM or 10 μM. Following 5 hr of LPS stimulation, supernatants were taken and TNF-α and IL-8 levels were determined by ELISA. In addition, cells treated with PBS or polypeptides, but not incubated with LPS, were removed at the time of supernatant removal to determine the viability of the cells following 7 hr of contact with the polypeptides. From the data depicted in FIG. 2, it can be seen that the SV40 polypeptide had no effect on TNF-α production but that the SV40MEM polypeptide inhibited TNF-α production in a dose-dependent manner. Similar results were obtained with respect to IL-8 production (data not shown).

EXAMPLE 3

Comparison of the Inhibition by the SV40MEM Polypeptide and other Inhibitory Polypeptides of κ Ig Light Chain Expression This experiment was conducted to compare the inhibitory effect of the SV40MEM polypeptide with that of the polypeptide AAVALLPAVLLALLAPVQRKRQKLMP (SEQ ID NO:5) (the "NF-κBMEM" polypeptide) on κ light chain expression in 70Z/3 B-cells.

The 70Z/3 cells were pretreated for 2 hr with between 0 and 50 μM of: (1) a peptide containing only the FGF signal sequence AAVALLPAVLLALLAP (SEQ ID NO:4) (the "MEM" peptide); (2) a polypeptide having the FGF signal sequence and the NLS of NF-κB p50 on the carboxy terminus of the signal sequence, namely, the NF-κBMEM polypeptide; (3) the SV40MEM polypeptide comprised of L-amino acids; or (4) the SV40MEM polypeptide comprised of D-amino acids. The cells were then incubated with LPS as described in Example 2 and assayed for expression of κ light chain expression.

Figure 3:
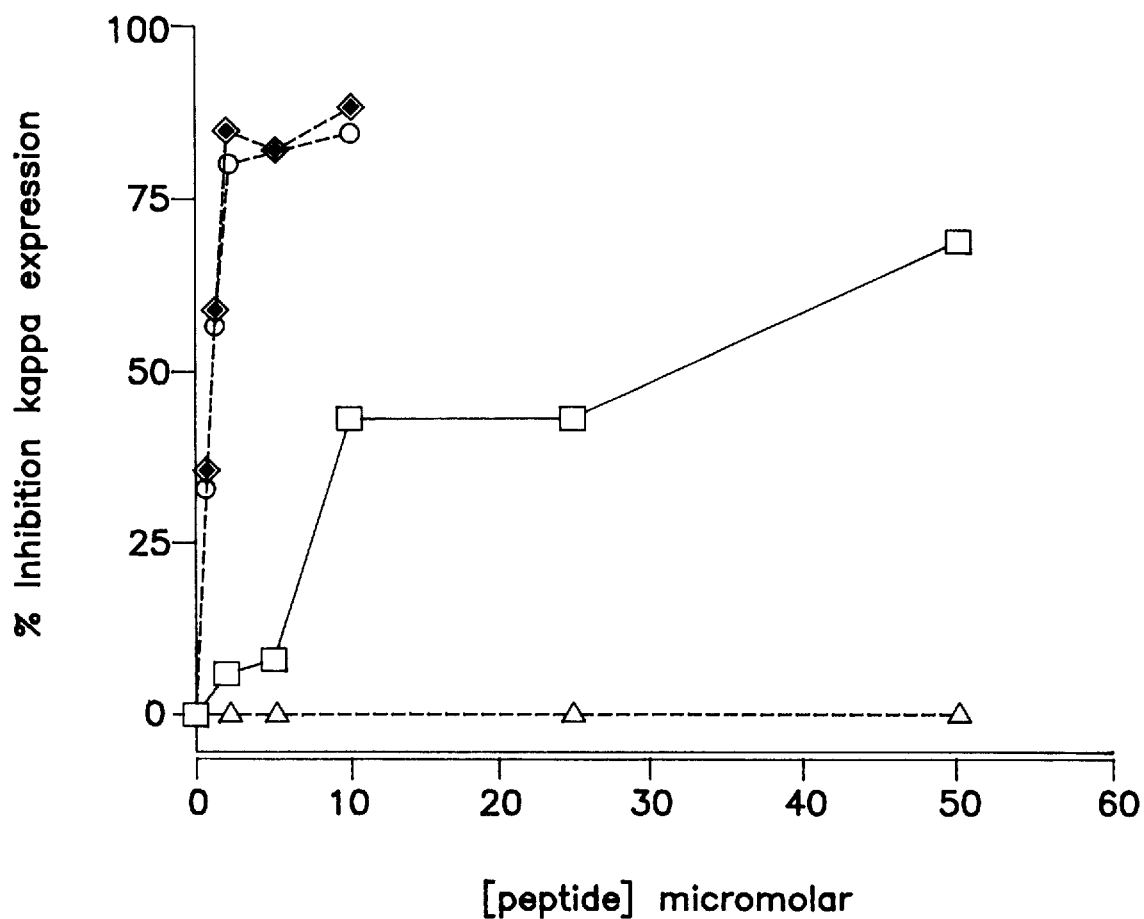
FIG. 3 is a graphical representation of dose-response relationships of three inhibitory polypeptides on LPS-stimulated κ Ig light chain production in 70Z/3 murine leukemia pre-B cells (triangles: a peptide containing only the fibroblast growth factor ("FGF") signal sequence AAVALLPAVLLALLAP (SEQ ID NO:4) (the "MEM" peptide); squares: a polypeptide having the FGF signal sequence and the NLS of NF-κB p50 on the carboxy terminus of the signal sequence, namely, AAVALLPAVLLALLAPVQRKRQKLMP (SEQ ID NO:5) polypeptide (the "NF-κBMEM" polypeptide); diamonds: the SV40MEM polypeptide comprised of L-amino acids; circles: the SV40MEM polypeptide comprised of D-amino acids.).

The data in FIG. 3 show that the L- and D-amino acid forms of the SV40MEM polypeptide were equally potent and efficacious with respect to inhibiting LPS-stimulated κ Ig expression. In addition, the data show that both the L- and D-amino acid forms of the SV40MEM polypeptide were more potent and more efficacious that the NF-κBMEM polypeptide having a single NLS sequence. The $EC_{50}$ for both the L- and D-amino acid forms of the SV40MEM polypeptide was 0.7 μM, while that for the NF-κBMEM polypeptide having a single NLS sequence was 32 μM.

EXAMPLE 4

Figure 4A:
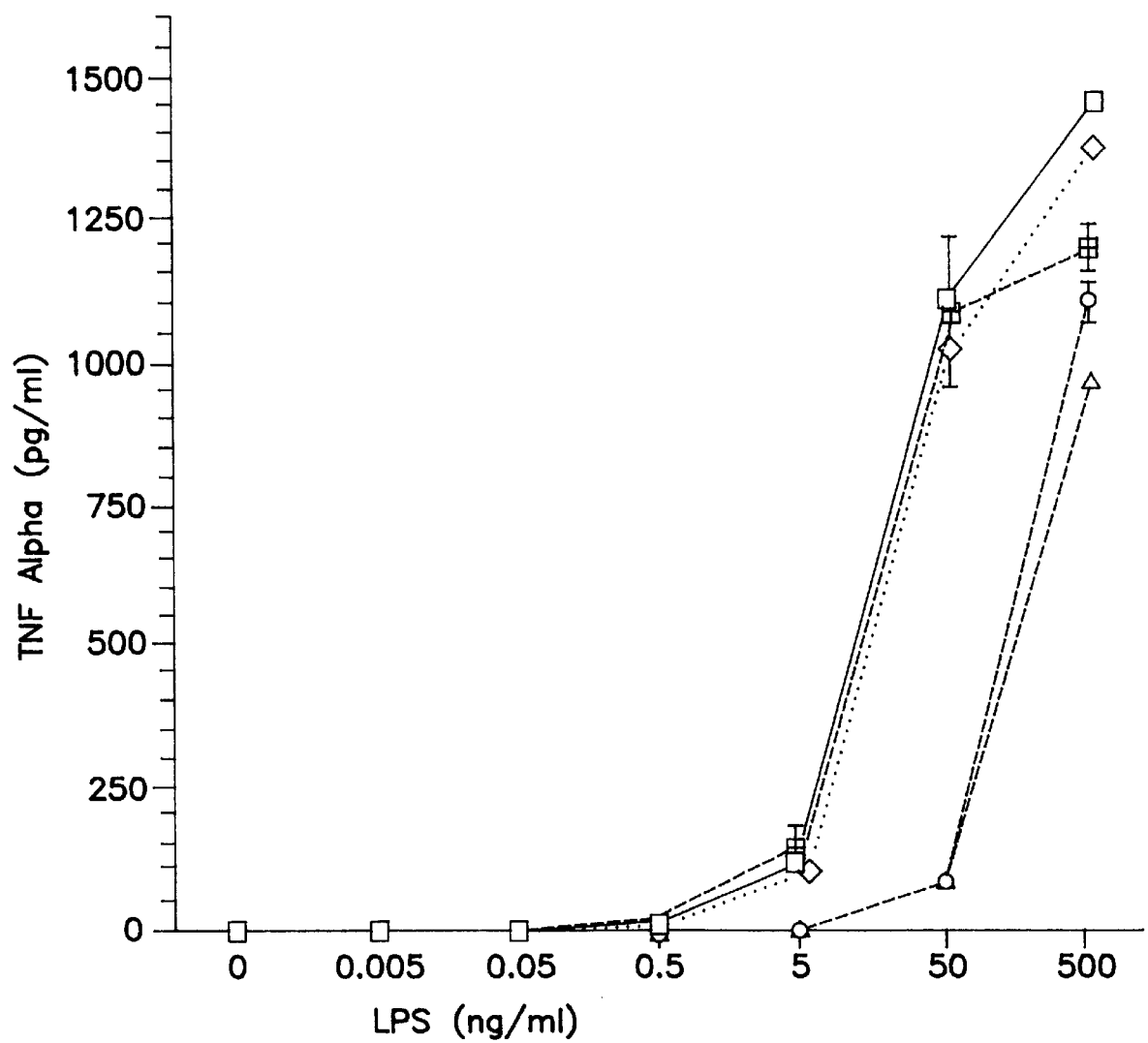
FIG. 4A is a graphical representation of the effect of inhibitory polypeptides on LPS-stimulated TNF-α production.
Figure 4B:
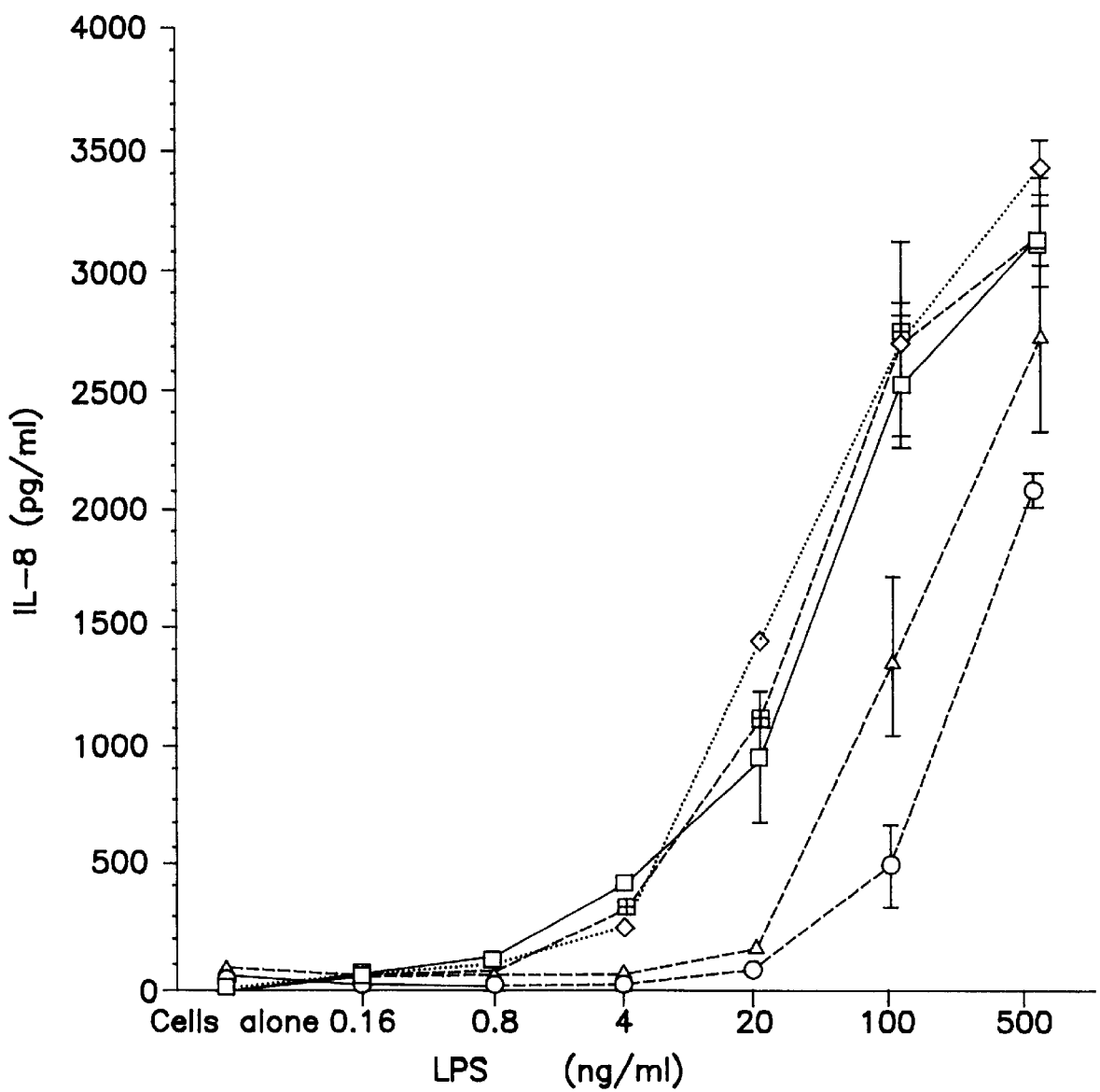
FIG. 4B is a graphical representation of the effect of inhibitory polypeptides on LPS-stimulated interleukin-8 ("IL-8") production. In both FIG. 4A and FIG. 4B the following symbols are used: squares—media control; crossed squares—the MEM peptide (5 μM); diamonds—the NF-κBMEM polypeptide (5 μM); circles—the SV40MEM polypeptide comprised of L-amino acids (5 μM); and triangles—the SV40MEM polypeptide comprised of D-amino acids (5 μM).

Comparison of the Inhibition by the SV40MEM Polypeptide Other Inhibitory Polypeptides of Cytokine Production This experiment was conducted to compare the inhibitory effect of the SV40MEM polypeptide and other inhibitory polypeptides on LPS induction of cytokine production. THP-1 control cells (ATCC 9/95 stock) were harvested, washed and set up in RPMI 1640, 10% fetal calf serum as described in Example B. The cells were incubated for 2 hr with PBS or (1) the FGF signal sequence, (2) a polypeptide having the FGF signal sequence and the NLS of NF-κB p50 on the carboxy terminus of the signal sequence, (3) the SV40MEM polypeptide comprised of L-amino acids, or (4) the SV40MEM polypeptide comprised of D-amino acids at a final concentration of 5 μM. The cells were then plated into a 96-well plate with 0.1 ml/well. The plate was then incubated for 2 hr at 37° C. in a 5% $CO_2$ atmosphere. Following the initial incubation, media or a titration of LPS was added to each of the wells in a volume of 0.01 ml/well. Following 5 hr of LPS stimulation, supernatants were taken and TNF-α levels were determined by ELISA. The date depicted in FIG. 4A indicated that only the L- or D-amino acid forms of the SV40MEM polypeptide significantly inhibited LPS-induced TNF-α expression; i.e., the polypeptide comprising the FGF signal sequence peptide and the NF-κB NLS did not significantly inhibit TNF-α expression. At high LPS concentrations, TNF-α was induced even in cells that had been incubated with the L- or D-amino acid forms of the SV40MEM polypeptide. Similar results were obtained with LPS-induced IL-8 production (FIG. 4B).

EXAMPLE 5

Effect of the SV40MEM Polypeptide on CD40 Expression

Figure 5A:
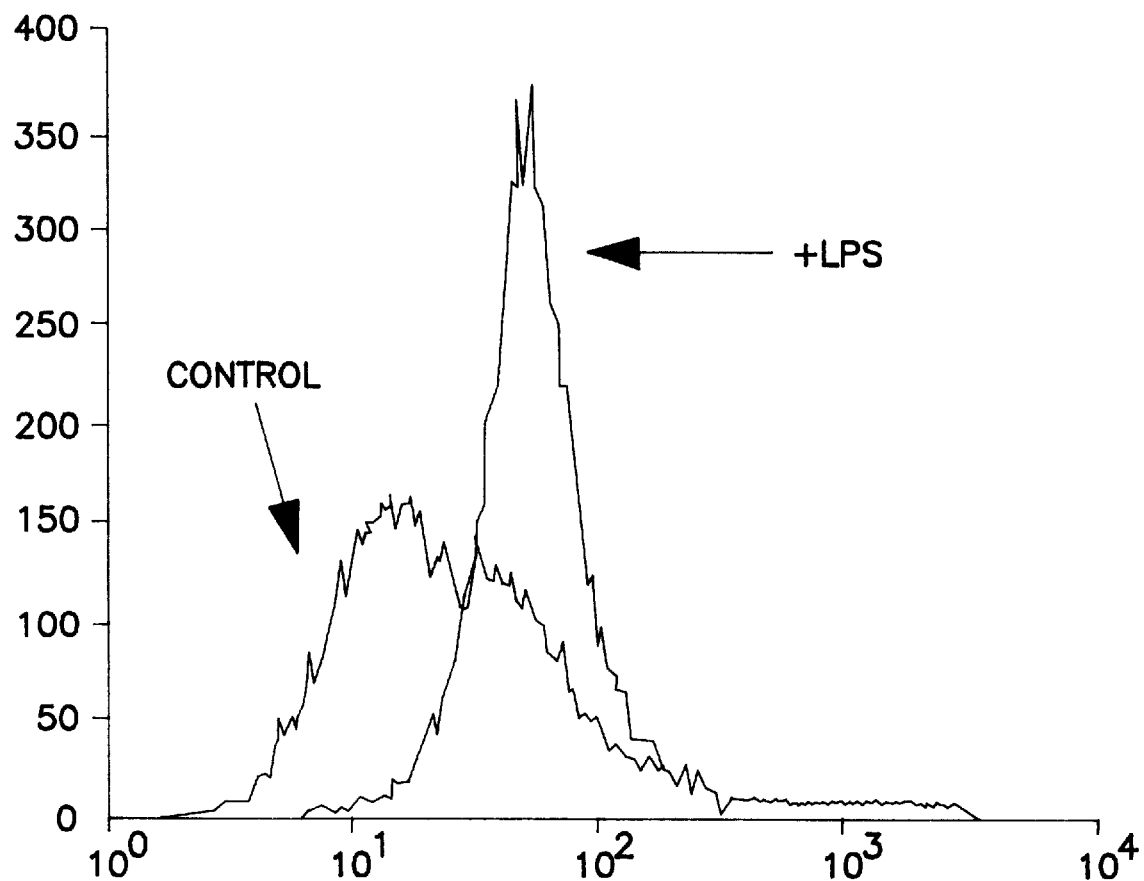
FIGS. 5A and 5B are graphical representation of the effect of the SV40MEM polypeptide on LPS-induced CD40 expression in 70Z/3 murine leukemia pre-B cells.
Figure 5B:
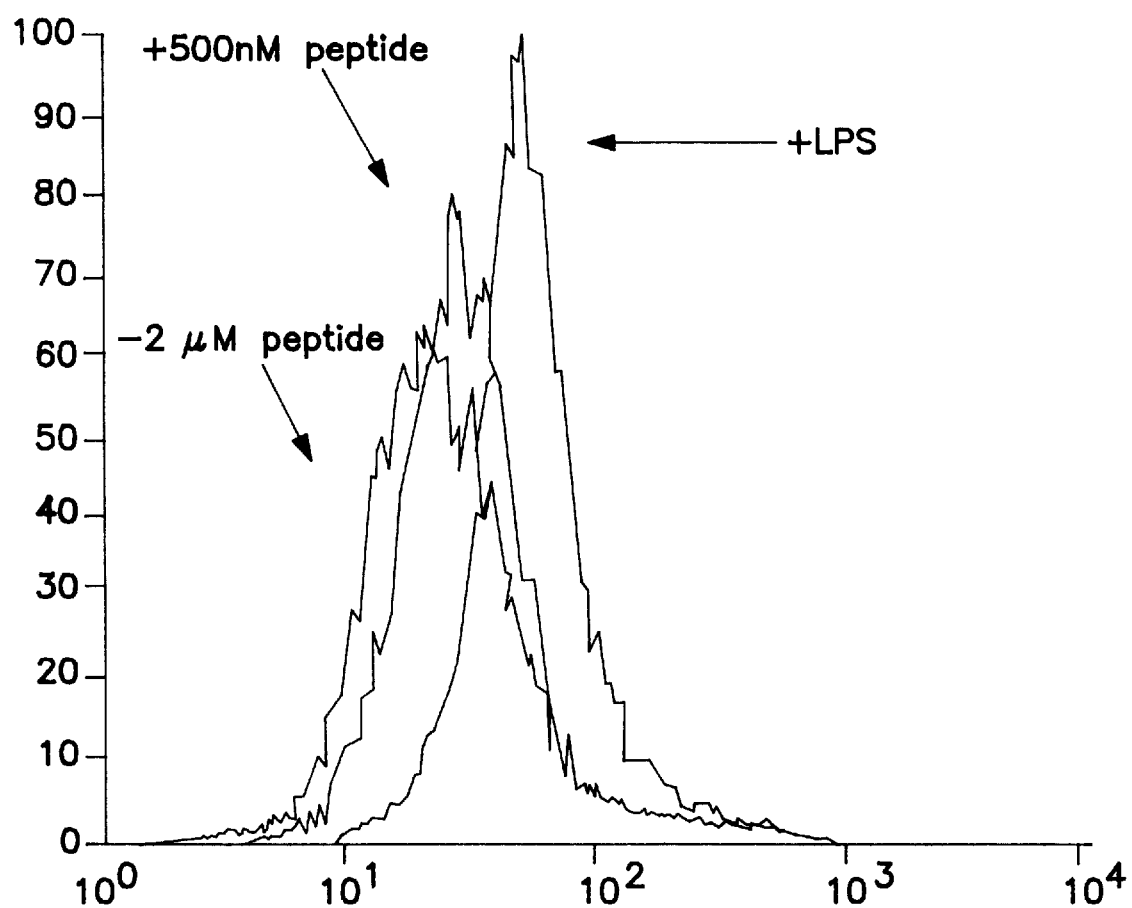
Figure 6A:
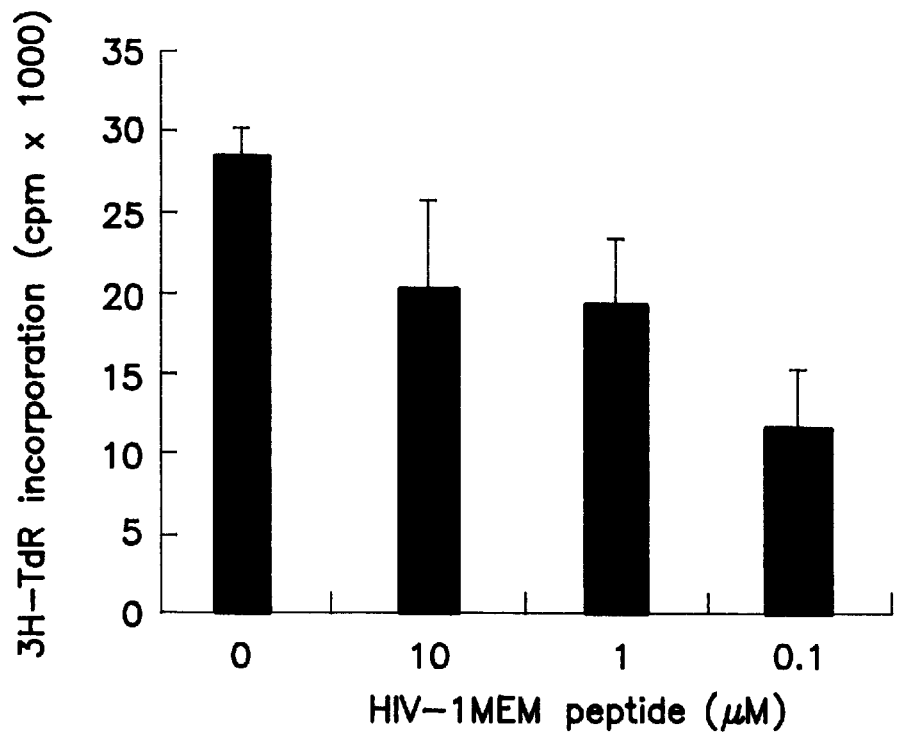
FIG. 6A is a graphical representation of the effect of the HIV-1MEM polypeptide on $^3$H-deoxyribothymidine uptake into peripheral blood mononuclear cells ("PBMCs").
Figure 6B:
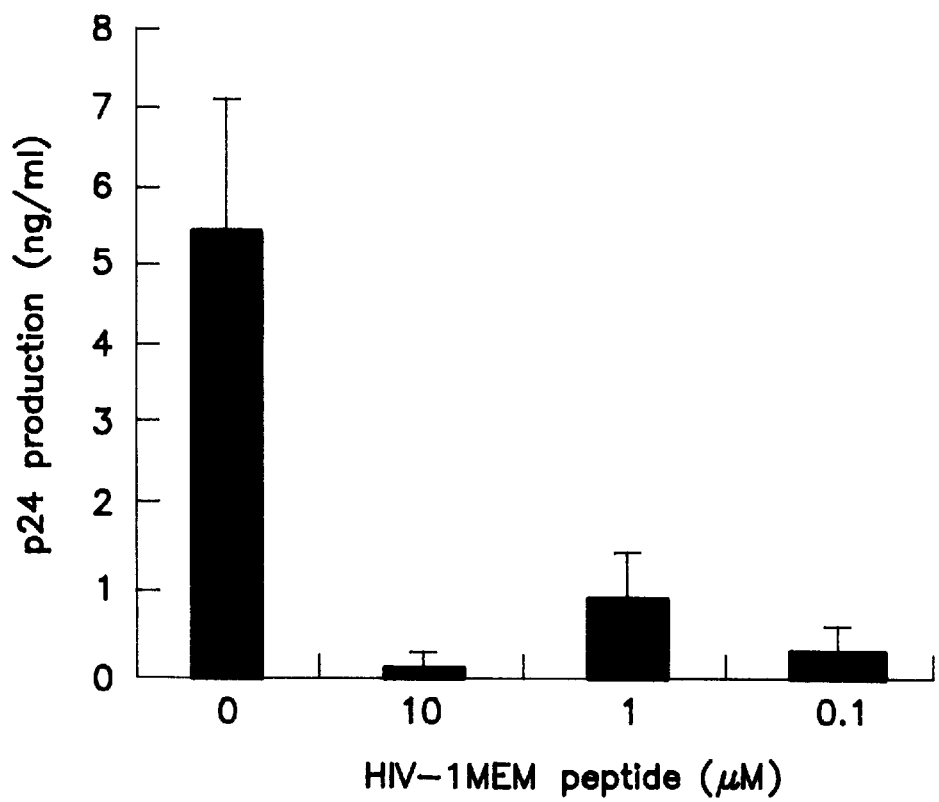
FIG. 6B is a graphical representation of the effect of HIV-1MEM on viral p24 production in anti-CD3 stimulated PBMCs infected with HIV-1 primary isolate M1.
Figure 6C:
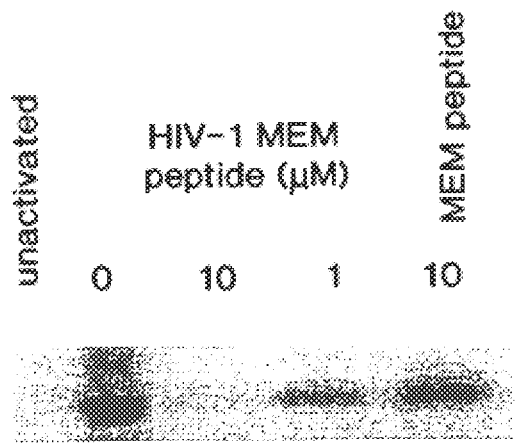
FIG. 6C is a photograph of a gel depicting the effect of HIV-1MEM polypeptide on the expression of proviral gag sequences in anti-CD3 activated PBMCs infected with HIV-1 primary isolate M1.
Figure 7:
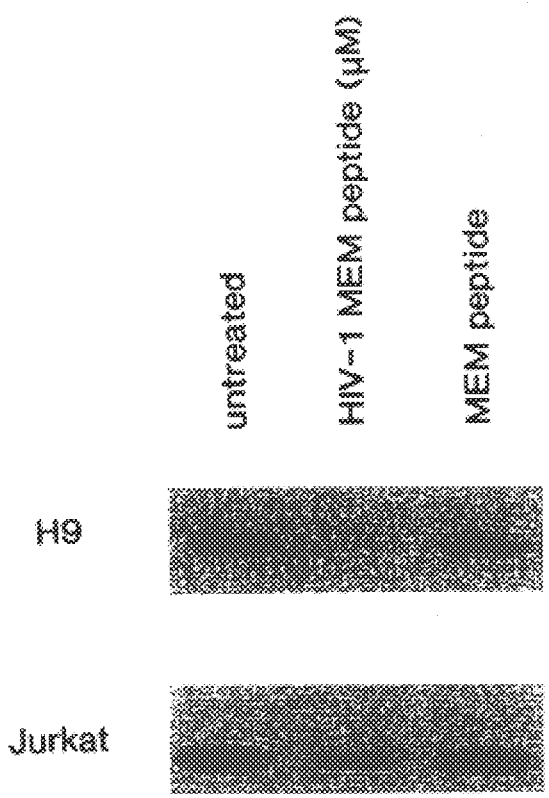
FIG. 7 is a photograph of a gel depicting the results of a polymerase chain reaction analysis of the effect of HIV-1MEM polypeptide on the expression of proviral gag sequences in H9 human lymphoma T-cells or Jurkat human leukemia T-cells infected with HIV-1 primary isolate M1.
Figure 8A:
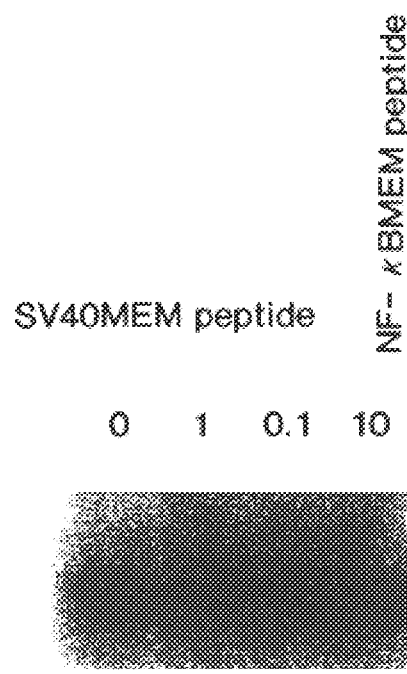
FIG. 8A is a photograph of gels depicting the results of polymerase chain analyses of the effect of HIV-1MEM and the NF-κBMEM polypeptide on the expression of proviral gag sequences in Jurkat T-cells infected with HIV$_{LAI}$.
Figure 8B:
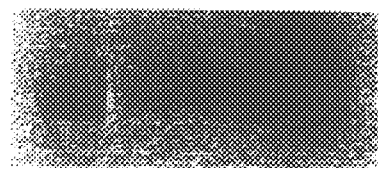
FIG. 8B is a photograph of gels depicting the results of polymerase chain analyses of the effect of HIV-1MEM and the NF-κBMEM polypeptide on the expression of 2-long terminal repeat ("LTR") circles in Jurkat T-cells infected with HIV$_{LAI}$.
Figure 9:
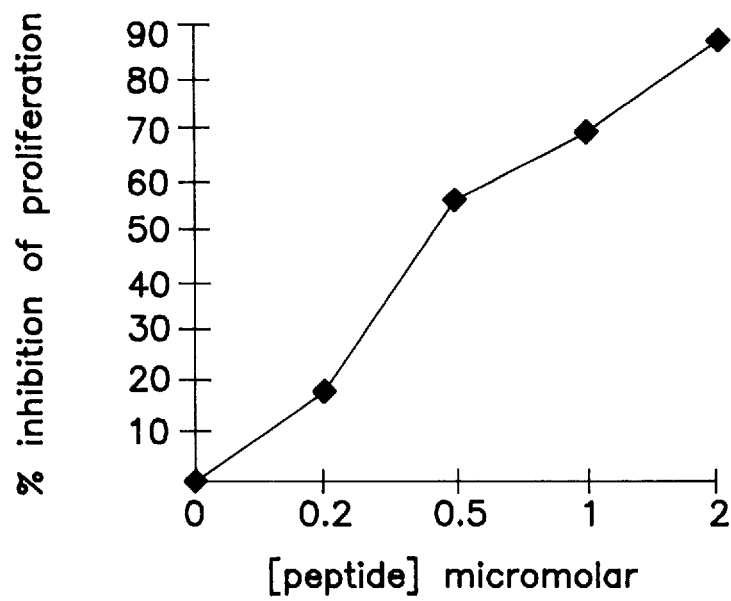
FIG. 9 is a graphical representation of the effect of SV40MEM prepared from D-amino acids on proliferation of 70Z/3 murine leukemia pre-B cells.
Figure 10:
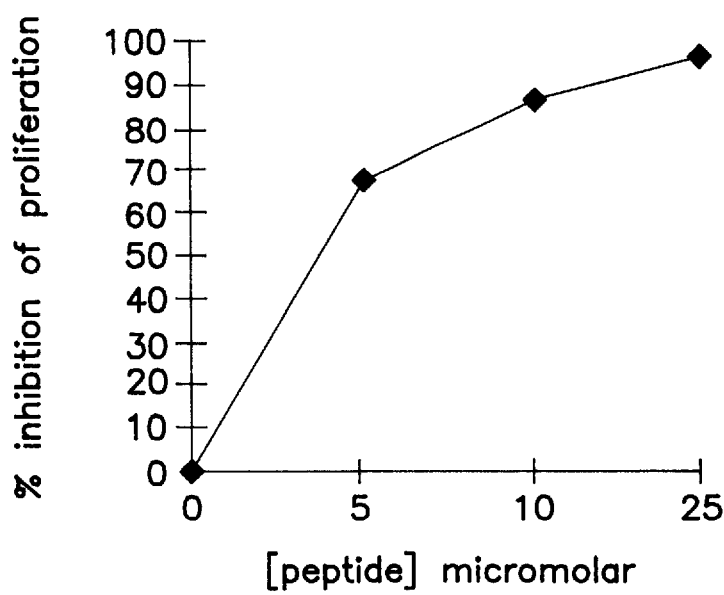
FIG. 10 is a graphical representation of the effect of SV40MEM prepared from D-amino acids on proliferation of RAJI human B-cell leukemia cell line.

70Z/3 murine B-cells were treated with the SV40MEM polypeptide for 3 hr prior to activation with LPS. After activation with LPS, there was an approximately four-fold increase in CD40 expression above basal levels. The SV40MEM polypeptide inhibited this up-regulation of CD40 (see FIGS. 5A and 5B). These results indicate that the SV40MEM polypeptide should be efficacious at inhibiting B-cell responses in vivo.

EXAMPLE 6

Inhibition of Infection of Peripheral Blood Mononuclear Cells with the Primary Isolate of HIV-1 M1 by the HIV-1MEM Polypeptide PBMCs were obtained washed, cultured, and infected with HIV-1 as described in Dubrovsky et al. (1995) *Mol. Med.* 1:217–230). PBMCs from a seronegative donor were collected and depleted of $CD8^+$ T cells by negative selection. The cells were activated with an anti-CD3 monoclonal antibody prepared according to the method described in Wee et al. (1993) *J. Exp. Med.* 177:219 and incubated for 3 hr with the HIV-1MEM polypeptide. The cells were then incubated with M1 virus isolated from PBMC collected from HIV-infected donors in the presence of inhibitors for 2 hr. The virus was washed out, and the cultures supplemented with the appropriate inhibitor and allowed to incubate for seven days. Virus production was determined by measuring the p24 levels in the culture supernatant (FIG. 6B) and contrasted with the effect of the polypeptide on cell proliferation (FIG. 6A), which virus load was determined by polymerase chain reaction analysis of proviral DNA content (gag) (FIG. 6C). The MEM peptide represents the FGF membrane translocating portion of the HIV-1MEM polypeptide. The HIV-1MEM polypeptide significantly reduced the virus load and virus production compared to untreated but activated cultures.

EXAMPLE 7

Inhibition of Infection of T Cells with $HIV_{M1}$ Virus by the HIV-1MEM Polypeptide H9 and Jurkat cells were incubated with the HIV-1MEM polypeptide (2 $\mu$M) or the control MEM peptide for 4 hr prior to addition of HIV-M1 virus. Cells were harvested on day 3 following injection and the level of HIV-1 DNA evaluated by polymerase chain reaction. As shown in FIG. 7, the HIV-1MEM polypeptide inhibited infection of both cells lines as determined by the lower levels of HIV-1 DNA compared to untreated and MEM peptide-treated cultures.

EXAMPLE 8

Reduction in Viral Infection Due to Reduction in Nuclear Translocation of HIV Genome Jurkat cells were incubated with the SV40MEM polypeptide for 3 hr with $HIV_{LAI}$ for 1–2 hr. The virus was washed out and the cultures supplemented with the appropriate inhibitor (SV40MEM, 0.1 $\mu$M and 1.0 $\mu$M; NF-κBMEM, 10 $\mu$M). After 24 hr, the cells were collected, lysed and evaluated for HIV-1 DNA by polymerase chain reaction analysis of gag sequences (see FIG. 8A) and 2-LTR circles (see FIG. 8B). The uniform signal achieved in all samples when assayed for gag sequences shows that all cultures internalized virus relatively equally and allowed formation of the viral cDNA in the cytoplasm. The difference in the levels of 2-LTR circles shows that SV40MEM inhibited translocation of the viral genome into the nucleus. Thus, the polypeptides do not affect virus entry into cells but, as predicted, specifically target nuclear translocation. The NF-κBMEM peptide showed no effect on viral internalization or translocation of the viral genome into the nucleus.

EXAMPLE 9

Effect of SV40MEM on Proliferation of 70Z/3 Murine B-cell Leukemia Cells

Murine 70Z/3 B-cells were treated with 0, 0.2, 0.5, 1, or 2 $\mu$M SV40MEM prepared from D-amino acids. On day 0, the cell concentrations of the control and treated cells were the same. After 48 hr of exposure to the peptide, the treated cells were again counted and compared to control cells. FIG. 9 shows that the proliferation of the murine leukemia cell line was inhibited by the lowest concentration (0.2 $\mu$M) of D-SV40MEM tested and was 90% inhibited by the highest concentration tested (2 $\mu$M).

EXAMPLE 10

Effect of SV40MEM on Proliferation of RAJI Human B-cell Leukemia Cells

Human RAJI B-cells were treated with 0, 5, 10 or 25 $\mu$M SV40MEM prepared from D-amino acids. On day 0, the cell concentrations of the control and treated cells were the same. After 48 hr of exposure to the peptide, the treated cells were again counted and compared to control cells. FIG. 10 shows that the proliferation of the murine leukemia cell line was inhibited by the lowest concentration (5 $\mu$M) of D-SV40MEM tested and was greater than 95% inhibited by the highest concentration tested (25 $\mu$M).

EXAMPLE 11

In Vivo Immunosuppressive Effect of the SV40MEM Polypeptide In a Murine Sheep Red Blood Cell Assay Female BALB/c mice (6–8 weeks of age) were housed in groups of 5 in Thorne units with ad libitum access to food and water. Mice were immunized on day 0 by intravenous (IV) injection of $1\times10^8$ sheep red blood cells ("SRBCs"). The mice were then divided into groups of five and control solutions or inhibitory peptides were administered at various doses, either by IV injection or orally ("PO") by gavage with a 24-gauge feeding tube and routes.

The SV40MEM polypeptide was administered either intravenously (IV) or orally (PO) with the following schedule: IV administration of 5 mg/kg on days 0, 1, 2, and 3; PO administration of 1 mg/kg on days 0, 1, 2, 3, and 4. After 14 days, the mice were bled from the orbital sinus and the level of anti-SRBC antibodies were measured in the serum by ELISA. Briefly, Immulon 2 plates (Dynatech) were coated with SRBC membrane antigen (*Anal. Biochem.* 82:362–371 (1978)) at 5 $\mu$g/ml in 0.05M carbonate/bicarbonate buffer (pH 9.6) and incubated overnight at 2°–8° C. Plates were blocked for 1-hr at room temperature with Specimen Diluent Concentrate (Genetic Systems, Redmond, Wash.) diluted 1:10 with distilled water. The plates were washed in phosphate-buffered saline and 0.05% Tween-20 ("PBS/Tween"). Serum samples were diluted in Specimen Diluent and incubated for 1 hr at room temperature. After washing the plates in PBS/Tween, goat anti-mouse IgG1-horse radish peroxidase-conjugated ("IgG1-HRP") antibody (Southern Biotechnology, Birmingham Ala.) was added at 1:5000 dilution and incubated for 1 hr at room temperature. Plates were washed and conjugate binding was detected using 3,3'5,5'-tetramethylbenzidine ("TMB") (Genetic Systems) as the substrate. TMB was added and incubated for 15 min at room temperature. The reaction was stopped by the addition of 3N $H_2SO_4$. Absorbance at 45 nm was recorded from duplicate samples using a microtiter plate reader (Bio Tek Instruments).

Figure 11A:
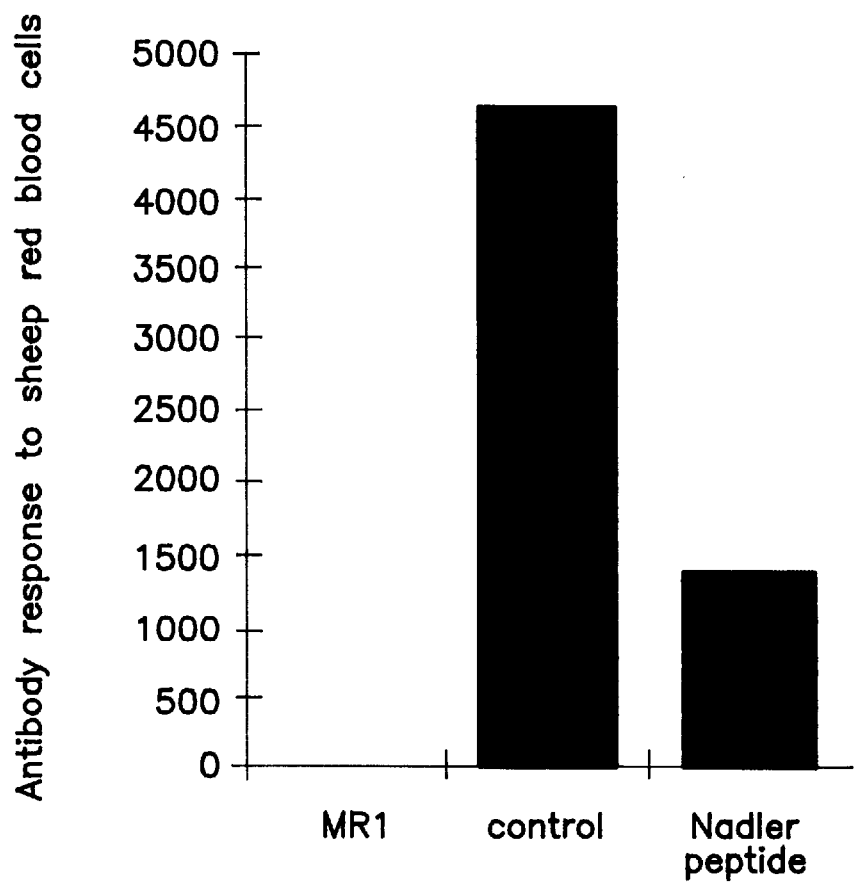
FIG. 11A is a graphical representation of the effect of an intravenous administration of the SV40MEM polypeptide on the in vivo response of mice to sheep red blood cells.
Figure 11B:
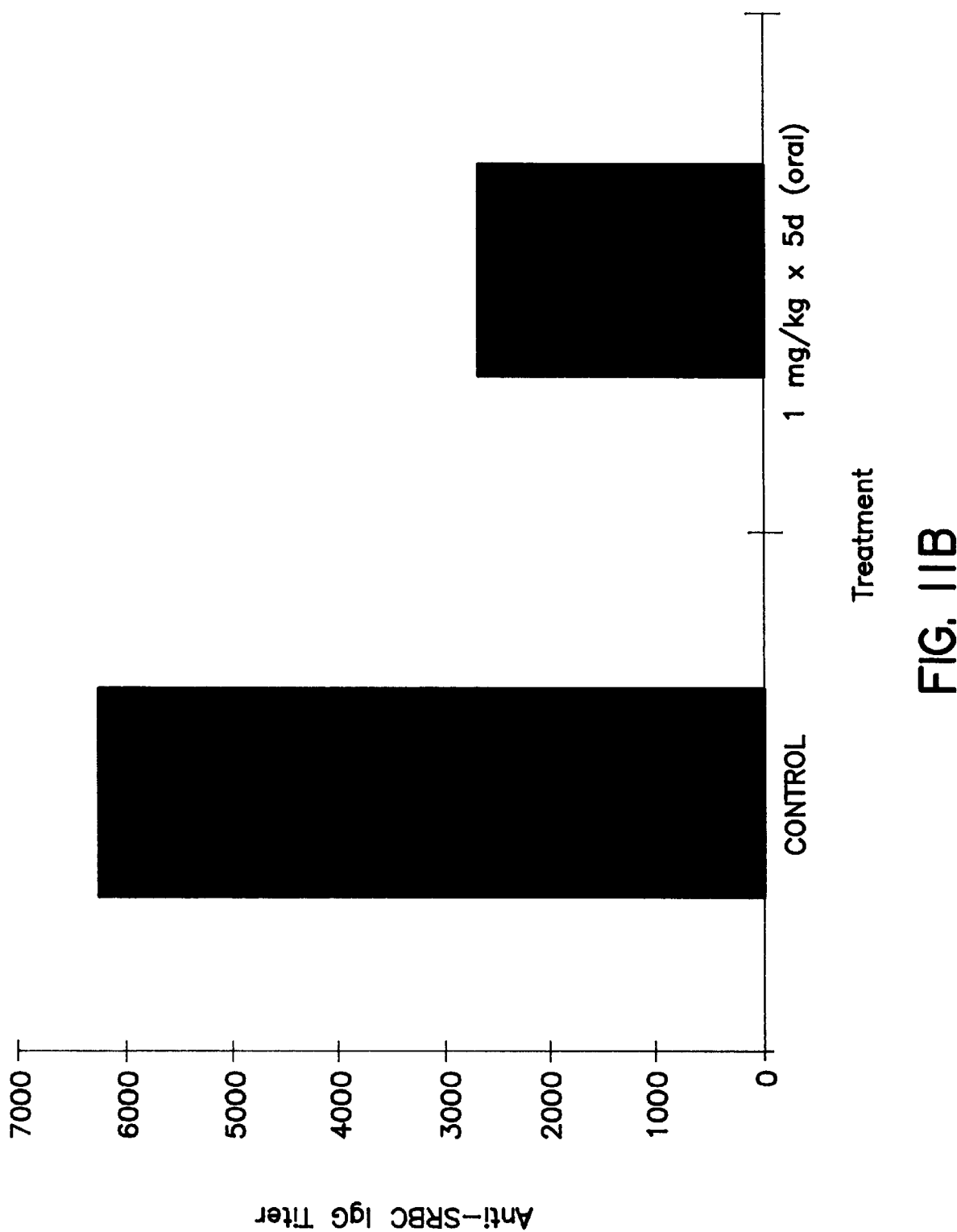
FIG. 11B is a graphical representation of the effect of an oral administration of the SV40MEM polypeptide on the in vivo response of mice to sheep red blood cells.

The results presented in FIG. 11A and FIG. 11B show that, while there was no effect on total IgG levels in the mice receiving the SV40MEM polypeptide either IV or PO, the polypeptide inhibited the specific anti-SRBC response when administered either IV or PO.

EXAMPLE 12

Comparison of the Inhibition by the BMS 205820 Polypeptide and other Inhibitory Polypeptides of the Anti-Hemocyanin Response in Mice Female BALB/c mice (8 weeks of age) were immunized by intraperitoneal injection of 25 µg keyhole limpet (*Megathura crenulata*) hemocyanin ("KLH") (Pacific Bio-Marine Laboratories, Venice, Calif.) without adjuvant on day 0. Mice were divided into groups of five and inhibitory peptides C-MYCMEM and BMS 205820 (PKKKRKVAAVALLPAVLLALLAPKKKRKV (SEQ ID NO:24)), which is identical to the SV40MEM polypeptide with the exception that the polypeptide lacks the C-terminal cysteine, were administered on day 0 at 5 mg/kg, followed by 5 subsequent doses of the same concentration every other day. Control mice were treated with a single 200-µg dose of Chimeric L6 antibody ("Chi L6"). After 14 days, the mice were bled from the orbital sinus and the level of anti-KLH antibodies were measured in the serum by ELISA as described in Example 11.

Figure 12:
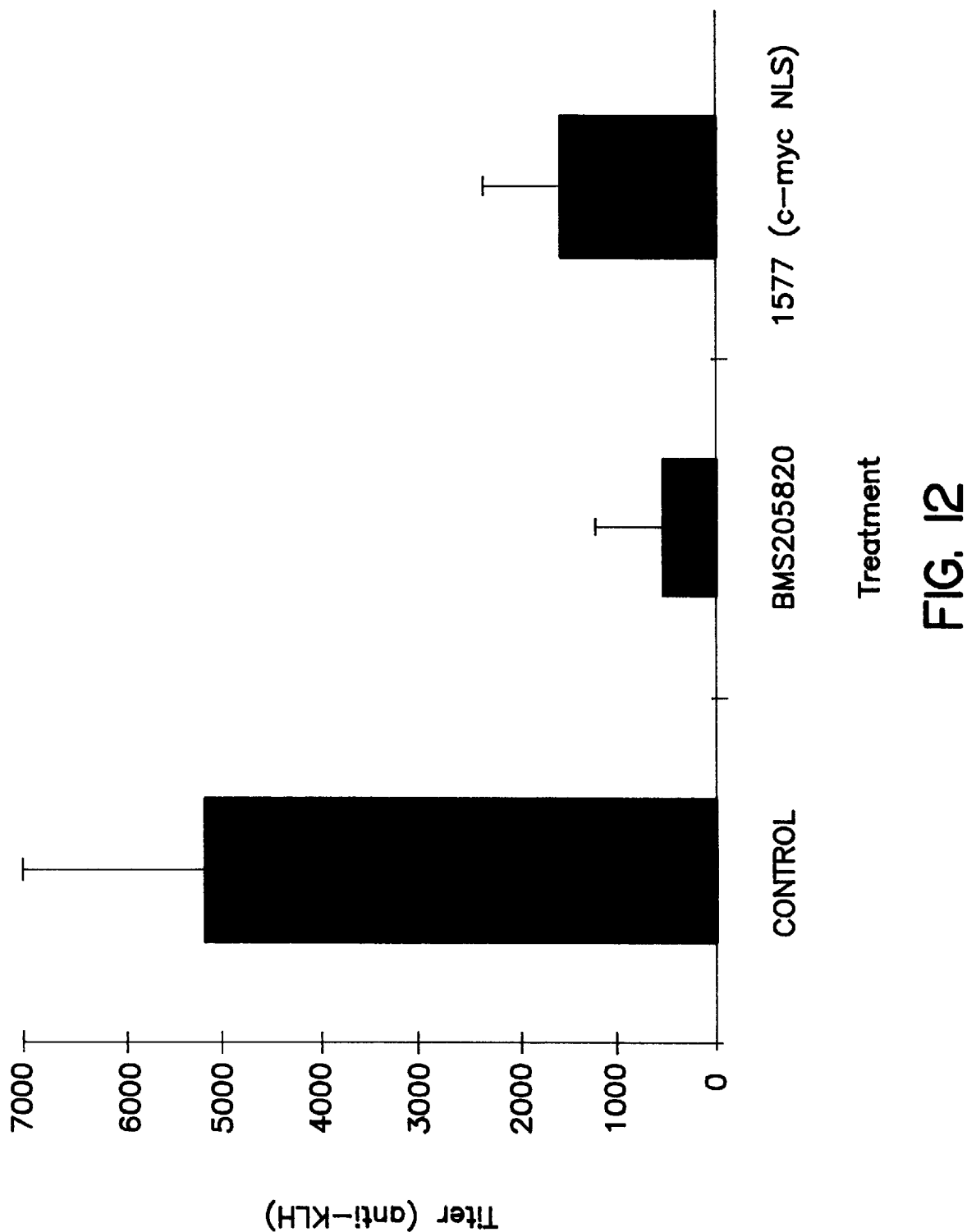
FIG. 12 shows the effect of BMS 205820 and C-MYCMEM (BMS 214572) on the anti-hemocyanin (KLH) response in mice.

Both the BMS 205820 and the C-MYCMEM polypeptide inhibited the specific anti-KLH response (see FIG. 12).

EXAMPLE 13

Stimulation of Apoptosis by the SV40MEM Polypeptide in Anti-CD3-treated Jurkat T-Cells A 24-hr incubation of Jurkat T-cells with SV40MEM and anti-CD3, caused greater than 85% of the cells to apoptose. Neither SV40MEM nor anti-CD3 alone caused significant apoptosis.

EXAMPLE 14

Inhibition of IκB Degradation by the SV40MEM Polypeptide

IκB is an inhibitor of NF-κB nuclear translocation. When cells are activated by the appropriate proinflammatory stimulus, e.g., cytokines or LPS, IκB is degraded. This results in the unmasking of the NLS of NF-κB, thereby allowing NF-κB to be translocated into the nucleus. This experiment was done to explore the effect of the SV40MEM polypeptide on IκB degradation in murine 70Z/3 cells.

Murine 70Z/3 cells (5×33 $10^7$ cells) were incubated with the SV40MEM polypeptide (2 µM) or PBS. The two groups of cells were subdivided into aliquots and activated with LPS (100 ng/ml) for 0, 15, 30, 60, or 120 min. The cells were lysed in 200 µL lysing buffer (20 mM N-(2-hydroxyethyl) piperazine-N'-(2-ethanesulfonic acid) ("HEPES"), pH 7.2, 20 mM NaCl, 2.5 mM $MgCl_2$, 0.1% nonylphenoxy polyethoxy ethanol ("NP-40")). The lysates were frozen until analyzed for the presence of IκB by Western analysis using an antibody directed to the carboxy terminus of IκB (Santa Cruz Corp., Santa Cruz, Calif.) according to the manufacturer's instructions.

Degradation of IκB was apparent after 15-min activation of the control cells with LPS. There was no apparent degradation of IκB in cells pretreated with the SV40MEM peptide.

EXAMPLE 15

Ability of BMS 205820 to Treat Septic Shock

These experiments show that BMS 205820 is efficacious for the treatment of septic shock. A lethal model of septic shock was used as follows.

A. Balb/c mice were pretreated with either 5 mg/kg BMS 205820 or PBS, intravenously at 1 and 3 hours, prior to injection with 200 mg lipopolysaccharide (LPS), the causative agent of septic shock. LPS was administered intraperitoneally. Mice were given another injection of the polypeptide immediately after the LPS injection, as well as 24 hours after the LPS injection. Mice typically died within 48 hours of the LPS injection.

As can be seen in Table 1, in two separate experiments, administration of BMS 205820 significantly increased the number of mice surviving seven days post-LPS injection.

TABLE 1

| | Fraction of Mice Surviving Seven Days Post LPS Injection | |
|---|---|---|
| Experiment | LPS + PBS | LPS + BMS 205820 |
| 1 | 0/10 | 6/10 |
| 2 | 2/10 | 10/10 |

B. Balb/c were treated with 200 µg of LPS followed by the BMS 205820 polypeptide, at the times indicated in Table 2. The BMS polypeptide was administered intravenously and the LPS was administered intraperitoneally. Group A mice were treated with 5 mg/kg of polypeptide in PBS at the indicated times, post-LPS administration. Group B mice received an additional dose of polypeptide 3 hours post-LPS treatment.

As can be seen in Table 2, BMS 205820 was effective in inhibiting death in response to LPS, especially when two doses of polypeptide were administered.

TABLE 2

| Effect of Delayed Treatment with BMS 205820 in a Lethal Model of Septic Shock | | |
|---|---|---|
| | Fraction Surviving | |
| Treatment | Group A | Group B |
| None | 0/5 | 2/5 |
| T = 0 | 5/5 | 5/5 |
| T = 30 min. | 1/5 | 5/5 |
| T = 1 hr. | 2/5 | 5/5 |
| T = 1.5 hr. | 1/5 | 4/5 |
| T = 2 hr. | 0/5 | 0/5 |

EXAMPLE 16

Inhibition of Cytokine Production in vivo by the BMS 205820 Polypeptide

These experiments show that the BMS 205820 polypeptide is capable of modulating cytokine production. In particular, a non-lethal model of septic shock was used. Balb/c mice were treated with 1 µg LPS, and at the same time, a single dose of 3 mg/kg of the BMS 205820 polypeptide in PBS. TNF-α, IL-6 and IL-10 levels were measured in serum by ELISA.

Figure 13A:
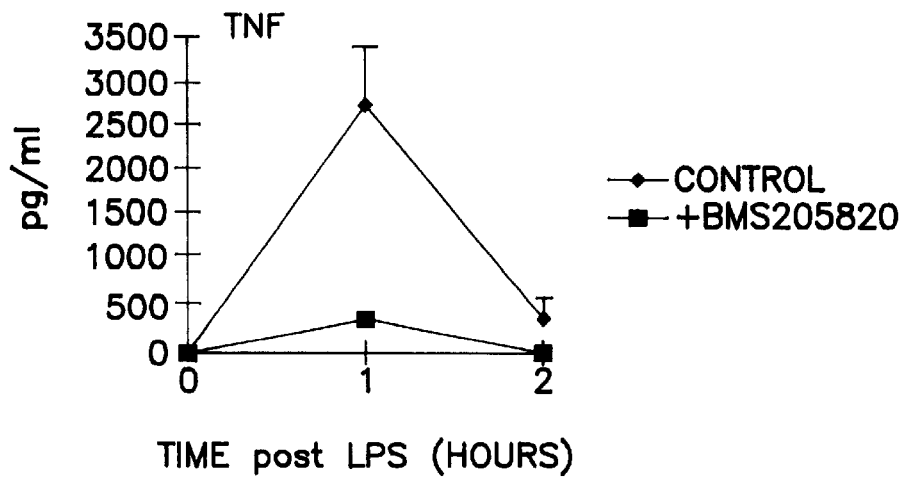
FIG. 13A, shows the effect of the BMS 205820 polypeptide on the production of TNF-α in vivo.
Figure 13B:
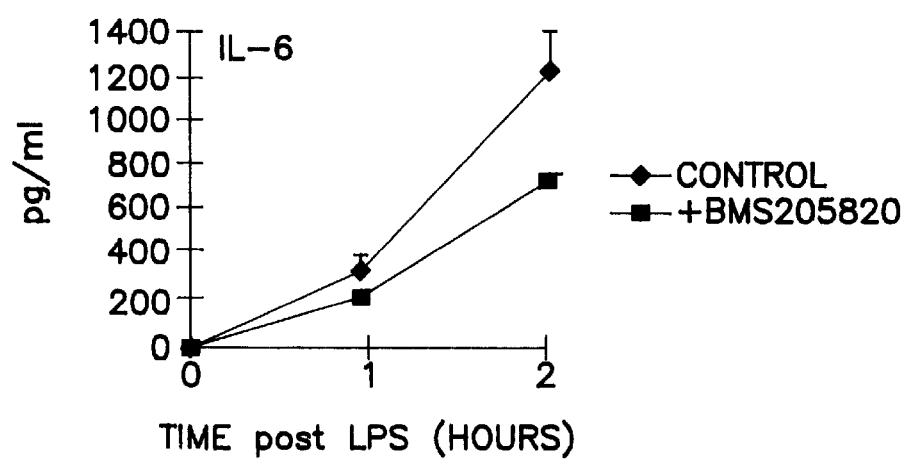
FIG. 13B shows the effect of the BMS 205820 polypeptide on the production of IL-6 in vivo.
Figure 13C:
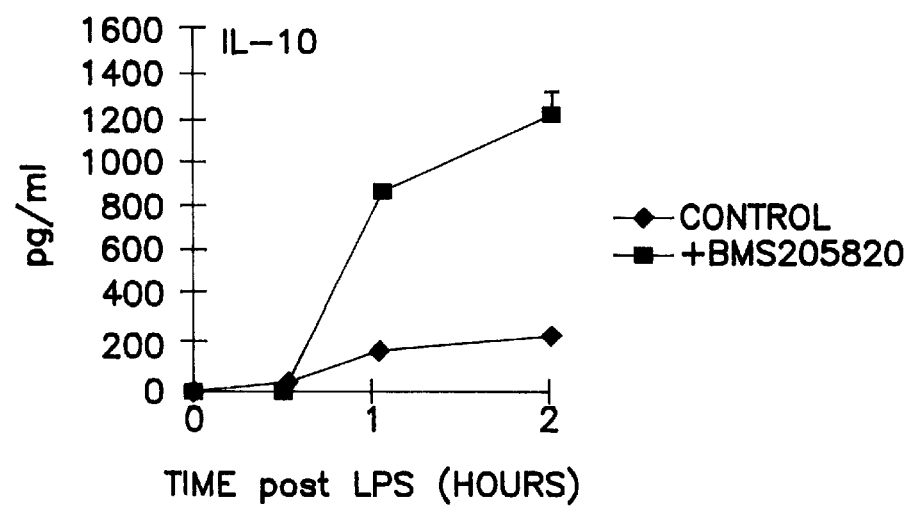
FIG. 13C shows the effect of the BMS 205820 polypeptide on the production of IL-10 in vivo.

As shown in FIG. 13A, the BMS 205820 polypeptide caused a significant inhibition in the production of TNF-α, which is a major contributor to the sepsis syndrome. IL-6 levels were only slightly affected (FIG. 13B), whereas IL-10 production was greatly increased (FIG. 13C). The effect on IL-10 is beneficial since this cytokine is immunosuppressive and has been shown to have efficacy in models of septic shock.

EXAMPLE 17

Inhibition of LPS Binding to CD14 Using BMS 205820 and C-MYCMEM

These experiments show that BMS 205820 and C-MYCMEM (the "BMS 214572" polypeptide) are both capable of inhibiting the binding of LPS to its cell surface receptor, CD14, evidencing that the polypeptide inhibitors are useful in the treatment of sepsis.

96-well plates were coated with goat-anti human Ig, soluble CD-14 Ig was added, and the plates were incubated overnight at 4° C. The BMS polypeptide, the C-MYCMEM polypeptide, an SV40 NLS polypeptide containing a single SV40 large T-antigen NLS, a c-myc NLS without a translocation sequence (AKRVKL (SEQ ID NO:6)), a control non-NLS polypeptide, 377G, or PBS, were added to the plates and the plates were incubated for 5 min. $E.$ $coli$ AO16 LPS was then added to the plates and the plates were incubated for 2 hours at 4° C. The plates were washed and LPS was detected using 0.5 μg/ml mouse anti-$E.$ $coli$ LPS, followed by goat anti-mouse horseradish peroxidase.

Figure 14:
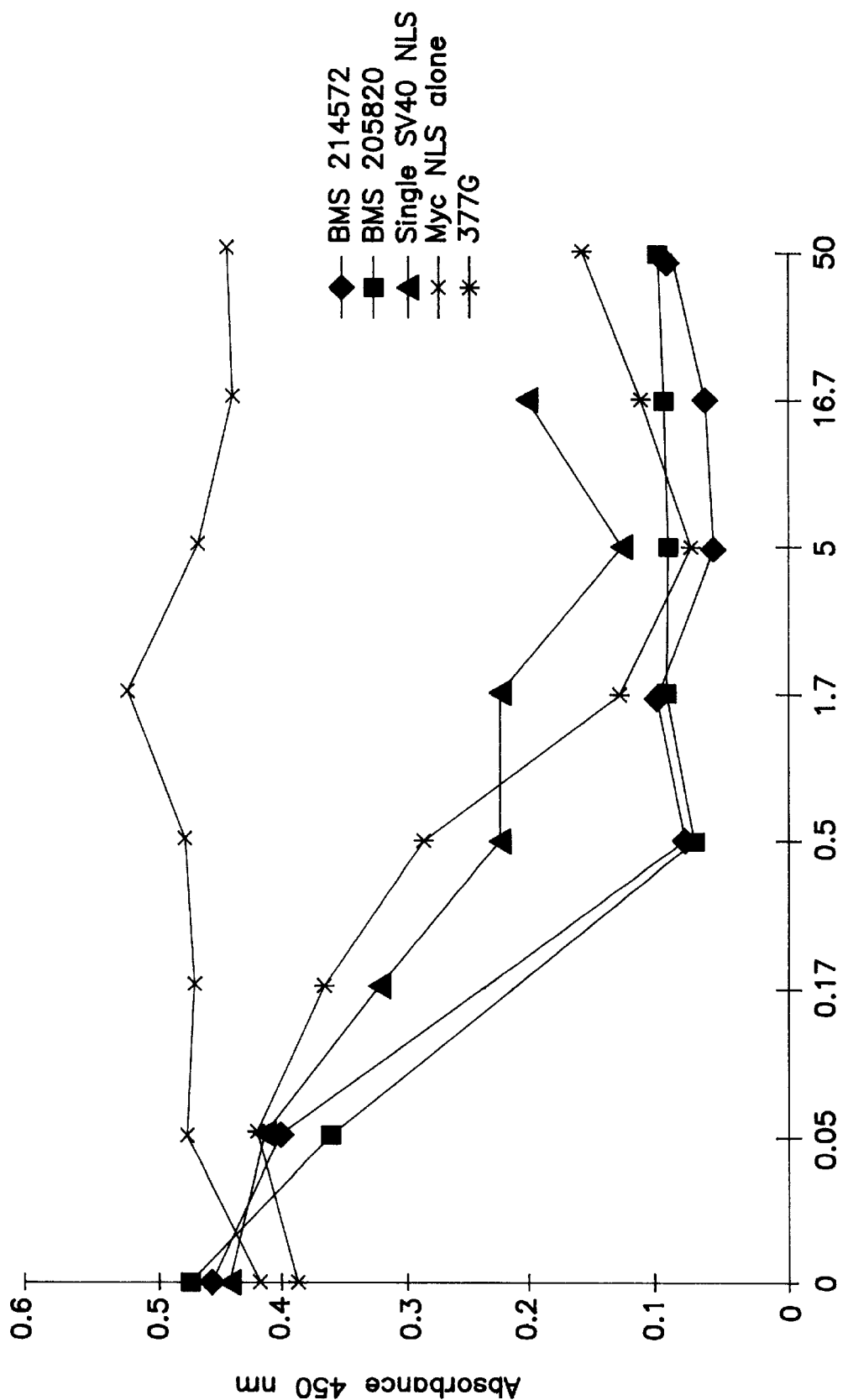
FIG. 14 depicts the effect of BMS 205820, C-MYCMEM (BMS 214572), an SV40 NLS polypeptide containing a single NLS, a c-myc NLS alone, without a translocation sequence (AKRVKL (SEQ ID NO:6)) and a control non-NLS polypeptide, 377G, on lipopolysaccharide (LPS) binding to CD14.

FIG. 14 shows the results of the experiment. Both BMS 205820 and C-MYCMEM were able to bind to LPS and block it from binding CD14. The c-myc NLS did not block binding of LPS to CD14.

LPS is the causative agent of septic shock. Thus, by blocking binding of LPS to CD14, the NLS polypeptides described herein may serve to prevent or diminish septic shock in vivo. This result was unexpected. Without being bound by a particular theory, it is possible that positively charged NLS polypeptides bind to negatively charged regions on LPS.

EXAMPLE 18

Ability of BMS 205820 to Treat Asthma

These experiments show that the BMS 205820 polypeptide is efficacious for the treatment of asthma. The BMS 205820 polypeptide was tested in a mouse model of asthma (Renz et al. (1992) *J. Allergy Clin. Path.* 89:1127–1138). Balb/c mice were administered ovalbumin in an alum adjuvant intraperitoneally at various times, as indicated in FIG. 15A. Treatment was followed by nebulization of ovalbumin into the lungs, also as indicated in FIG. 15A. The mice were also treated with 3 mg/kg of the BMS 205820 polypeptide in PBS at the times indicated. Mice were sacrificed at day 18 and the presence of eosinophils assayed. As seen in FIG. 15B, the BMS 205820 polypeptide significantly inhibited the infiltration of eosinophils into the lungs, a measure of the asthmatic state.

Thus, inhibitors of nuclear translocation of cellular proteins have been disclosed. Although preferred embodiments of the subject invention have been described in some detail, it is understood that obvious variations can be made without departing from the spirit and the scope of the invention as defined by the appended claims.

---

We claim:

1. An isolated polypeptide comprising:
(1) a signal sequence peptide capable of delivering the polypeptide through the cytoplasmic membrane into a cell; and
(2) at least two nuclear localization sequences (NLSs), wherein said polypeptide is capable of inhibiting nuclear translocation of a cellular protein.

2. The polypeptide of claim 1, wherein the signal sequence is interchangeably flanked at its amino- and carboxy-termini by first and second NLSs.

3. The polypeptide of claim 2, wherein the signal sequence peptide is the antennapedia homeodomain signal sequence peptide, the fibroblast growth factor signal sequence peptide, the human immunodeficiency virus (HIV) Tat signal sequence peptide, or the Hsc70 signal sequence peptide.

4. The polypeptide of claim 3, wherein the signal sequence peptide is the antennapedia homeodomain signal sequence peptide.

5. The polypeptide of claim 4, wherein the signal sequence peptide comprises the amino acid sequence RQIKIWFQNRRMKWKK (SEQ ID NO:7).

6. The polypeptide of claim 3, wherein the signal sequence peptide is the fibroblast growth factor signal sequence peptide.

7. The polypeptide of claim 6, wherein the signal sequence peptide comprises the amino acid sequence AAVALLPAVLLALLA (SEQ ID NO:8).

8. The polypeptide of claim 3, wherein the signal sequence peptide is the HIV Tat signal sequence peptide.

9. The polypeptide of claim 8, wherein the signal sequence peptide comprises the amino acid sequence CFITKALGISYGRKKRRQRRRPPQGSQTH (SEQ ID NO:9).

10. The polypeptide of claim 2, wherein the first and second NLSs may be the same or different and are peptides comprising the amino acid sequence selected from the group consisting of PKKKRKV (SEQ ID NO:10), KKKRKVC (SEQ ID NO:11), GKKRSKA (SEQ ID NO:12), KRPRP (SEQ ID NO:13), GNKAKRQRST (SEQ ID NO:14), GGAAKRVKLD (SEQ ID NO:15), SALIKKKKKMAP (SEQ ID NO:16), RKLKKLGN (SEQ ID NO:17), PQP-KKKP (SEQ ID NO:18), ASKSRKRKL (SEQ ID NO:19), KKKYK (SEQ ID NO:20), KKKYKC (SEQ ID NO:21), KSKKK (SEQ ID NO:22), KRVKLC (SEQ ID NO:23), and AKRVKL (SEQ ID NO:6).

11. The polypeptide of claim 7, wherein the first and second NLSs may be the same or different and are peptides comprising the amino acid sequence selected from the group consisting of PKKKRKV (SEQ ID NO:10), KKKRKVC (SEQ ID NO:11), GKKRSKA (SEQ ID NO:12), KRPRP (SEQ ID NO:13), GNKAKRQRST (SEQ ID NO:14), GGAAKRVKLD (SEQ ID NO:15), SALIKKKKMAP (SEQ ID NO:16), RKLKKLGN (SEQ ID NO:17), PQPKKKP (SEQ ID NO:18), ASKSRKRKL (SEQ ID NO:19), KKKYK (SEQ ID NO:20), KKKYKC (SEQ ID NO:21), KSKKK (SEQ ID NO:22), KRVKLC (SEQ ID NO:23), and AKRVKL (SEQ ID NO:6).

12. The polypeptide of claim 11, wherein the first and second NLSs comprise the amino acid sequence PKKKRKV (SEQ ID NO:10).

13. The polypeptide of claim 11, wherein the first and second NLSs comprise the amino acid sequence PKKKRKV (SEQ ID NO:10) and KKKRKVC (SEQ ID NO:11), respectively, KKKYK (SEQ ID NO:20) and KKKYKC (SEQ ID NO:21), respectively, or AKRVKL (SEQ ID NO:6) and KRVKLC (SEQ ID NO:23), respectively.

14. The polypeptide of claim 12 comprising the amino acid sequence PKKKRKVAAVALLPAVLLALLAP-KKKRKV (SEQ ID NO:24).

15. The polypeptide of claim 13 comprising the amino acid sequence PKKKRKVAAVALLPAVLLALLAP-KKKRKVC (SEQ ID NO:1).

16. The polypeptide of claim 1, wherein the cellular protein is a transcription factor.

17. The polypeptide of claim 16, wherein the transcription factor is NF-κB.

* * * * *

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Pro  Lys  Lys  Lys  Arg  Lys  Val  Ala  Ala  Val  Ala  Leu  Leu  Pro  Ala  Val
1                   5                        10                            15

Leu  Leu  Ala  Leu  Leu  Ala  Pro  Lys  Lys  Lys  Arg  Lys  Val  Cys
                    20                   25                       30
```

( 2 ) INFORMATION FOR SEQ ID NO:2:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Lys Lys Lys Tyr Lys Ala Ala Val Ala Leu Leu Pro Ala Val Leu Leu
1               5                           10                          15

Ala Leu Leu Ala Lys Lys Lys Tyr Lys Cys
                20              25

(2) INFORMATION FOR SEQ ID NO:3:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Ala Lys Arg Val Lys Leu Ala Ala Val Ala Leu Leu Pro Ala Val Leu
1               5                           10                          15

Leu Ala Leu Leu Ala Lys Arg Val Lys Leu Cys
                20              25

(2) INFORMATION FOR SEQ ID NO:4:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Ala Ala Val Ala Leu Leu Pro Ala Val Leu Leu Ala Leu Leu Ala Pro
1               5                           10                          15

(2) INFORMATION FOR SEQ ID NO:5:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Ala Ala Val Ala Leu Leu Pro Ala Val Leu Leu Ala Leu Leu Ala Pro
1               5                           10                          15

Val Gln Arg Lys Arg Gln Lys Leu Met Pro
                20              25

(2) INFORMATION FOR SEQ ID NO:6:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Ala Lys Arg Val Lys Leu
1               5

(2) INFORMATION FOR SEQ ID NO:7:

( i ) SEQUENCE CHARACTERISTICS:
    ( A ) LENGTH: 16 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:7:

```
Arg Gln Ile Lys Ile Trp Phe Gln Asn Arg Arg Met Lys Trp Lys Lys
1               5                   10                  15
```

( 2 ) INFORMATION FOR SEQ ID NO:8:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

```
Ala Ala Val Ala Leu Leu Pro Ala Val Leu Leu Ala Leu Leu Ala
1               5                   10                  15
```

( 2 ) INFORMATION FOR SEQ ID NO:9:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

```
Cys Phe Ile Thr Lys Ala Leu Gly Ile Ser Tyr Gly Arg Lys Lys Arg
1               5                   10                  15

Arg Gln Arg Arg Arg Pro Pro Gln Gly Ser Gln Thr His
                20                  25
```

( 2 ) INFORMATION FOR SEQ ID NO:10:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

```
Pro Lys Lys Lys Arg Lys Val
1               5
```

( 2 ) INFORMATION FOR SEQ ID NO:11:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

```
Lys Lys Lys Arg Lys Val Cys
1               5
```

( 2 ) INFORMATION FOR SEQ ID NO:12:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

```
Gly  Lys  Lys  Arg  Ser  Lys  Ala
1                    5
```

( 2 ) INFORMATION FOR SEQ ID NO:13:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

```
Lys  Arg  Pro  Arg  Pro
1                    5
```

( 2 ) INFORMATION FOR SEQ ID NO:14:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

```
Gly  Asn  Lys  Ala  Lys  Arg  Gln  Arg  Ser  Thr
1                    5                         10
```

( 2 ) INFORMATION FOR SEQ ID NO:15:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

```
Gly  Gly  Ala  Ala  Lys  Arg  Val  Lys  Leu  Asp
1                    5                         10
```

( 2 ) INFORMATION FOR SEQ ID NO:16:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:16:

```
Ser  Ala  Leu  Ile  Lys  Lys  Lys  Lys  Lys  Met  Ala  Pro
1                    5                         10
```

( 2 ) INFORMATION FOR SEQ ID NO:17:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

Arg  Lys  Leu  Lys  Lys  Leu  Gly  Asn
    1                          5

( 2 ) INFORMATION FOR SEQ ID NO:18:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:18:

Pro  Gln  Pro  Lys  Lys  Lys  Pro
    1                       5

( 2 ) INFORMATION FOR SEQ ID NO:19:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:19:

Ala  Ser  Lys  Ser  Arg  Lys  Arg  Lys  Leu
    1                       5

( 2 ) INFORMATION FOR SEQ ID NO:20:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:20:

Lys  Lys  Lys  Tyr  Lys
    1                     5

( 2 ) INFORMATION FOR SEQ ID NO:21:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:21:

Lys  Lys  Lys  Tyr  Lys  Cys
    1                     5

(2) INFORMATION FOR SEQ ID NO:22:

(i) SEQUENCE CHARACTERISTICS:
(A) LENGTH: 5 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:22:

Lys Ser Lys Lys Lys
1               5

(2) INFORMATION FOR SEQ ID NO:23:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:23:

Lys Arg Val Lys Leu Cys
1               5

(2) INFORMATION FOR SEQ ID NO:24:

(i) SEQUENCE CHARACTERISTICS:
(A) LENGTH: 29 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:24:

Pro Lys Lys Lys Arg Lys Val Ala Ala Val Ala Leu Leu Pro Ala Val
1               5                       10                      15

Leu Leu Ala Leu Leu Ala Pro Lys Lys Lys Arg Lys Val
            20                  25